(12) United States Patent
Phillips

(10) Patent No.: US 12,280,040 B2
(45) Date of Patent: Apr. 22, 2025

(54) COMPOSITIONS AND METHODS OF A DIHYDROISOXAZOLE COMPOUND THAT REDUCES ECTOPARASITE INFESTATIONS ON FISH

(71) Applicant: EVAH Atlantic Inc., Charlottetown (CA)

(72) Inventor: Lisa Michele Phillips, Charlottetown (CA)

(73) Assignee: EVAH Atlantic Inc., Charlottetown (CA)

( * ) Notice: Subject to any disclaimer, the term of this patent is extended or adjusted under 35 U.S.C. 154(b) by 0 days.

(21) Appl. No.: 18/884,300

(22) Filed: Sep. 13, 2024

(65) Prior Publication Data

US 2025/0090503 A1    Mar. 20, 2025

Related U.S. Application Data

(60) Provisional application No. 63/538,786, filed on Sep. 15, 2023, provisional application No. 63/610,853, filed on Dec. 15, 2023.

(51) Int. Cl.
*C07D 413/04* (2006.01)
*A23K 20/137* (2016.01)
(Continued)

(52) U.S. Cl.
CPC .......... *A61K 31/422* (2013.01); *A23K 20/137* (2016.05); *A23K 50/80* (2016.05); *A61K 9/0056* (2013.01); *A61P 33/14* (2018.01)

(58) Field of Classification Search
CPC .. A61K 31/422; A61K 9/0056; A23K 20/137; A23K 50/80; A61P 33/14
(Continued)

(56) References Cited

U.S. PATENT DOCUMENTS

| 8,389,659 B2 | 2/2013 | Nanchen et al. |
| 9,538,758 B2 | 1/2017 | Johannessen |

(Continued)

FOREIGN PATENT DOCUMENTS

| CA | 2747354 A1 | 6/2010 |
| CA | 2747354 C | 6/2010 |

(Continued)

OTHER PUBLICATIONS

Emont, "Salmon's Getting More Expensive. Blame Bloodsucking Sea Lice.," Wall Street Journal, 6 pages (2024).
(Continued)

*Primary Examiner* — Brent T O'Hern
(74) *Attorney, Agent, or Firm* — Finnegan, Henderson, Farabow, Garrett & Dunner, LLP

(57) ABSTRACT

Ectoparasite infestations in fish farming can pose significant challenges and issues for aquaculture operations. This disclosure generally relates to treatment or control of ectoparasite infestations (such as sea lice infestations) on fish (such as salmonids) using a particular dosing regimen of an isoxazoline. In particular, the dosing regimen includes oral administration of the active ingredient:

(S)-3-methyl-N-(2-oxo-2-(prop-2-yn-1-ylamino) ethyl)-5-(5-(3,4,5-trichlorophenyl)-5-(trifluoromethyl)-4,5-
(Continued)

dihydroisoxazol-3-yl) thiophene-2-carboxamide, including salts, or N-oxide, or solvates thereof, of structural formula

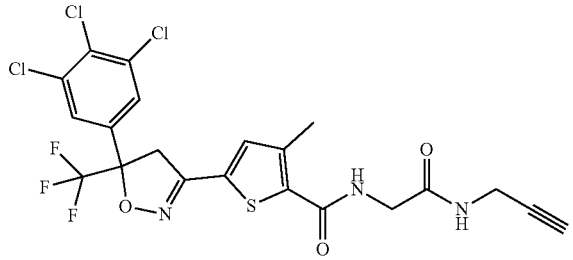

The active ingredient may be administered at a dosage (i.e., in a dose) of from about 0.025 mg/kg/d to about 0.250 mg/kg/d. The dosing regimen may include oral administration from about 3 to about 10 consecutive days.

13 Claims, 8 Drawing Sheets

(51) Int. Cl.
*A23K 50/80* (2016.01)
*A61K 9/00* (2006.01)
*A61K 31/422* (2006.01)
*A61P 33/14* (2006.01)

(58) Field of Classification Search
USPC .............................................................. 426/2
See application file for complete search history.

(56) References Cited

U.S. PATENT DOCUMENTS

| | | | |
|---|---|---|---|
| 9,920,037 B2* | 3/2018 | Gauvry | A01N 43/80 |
| 10,040,785 B2 | 8/2018 | Gauvry et al. | |
| 10,537,549 B2 | 1/2020 | Tahtaoui | |

FOREIGN PATENT DOCUMENTS

| | | |
|---|---|---|
| CA | 2 882 199 A1 | 3/2014 |
| CA | 2963472 A1 | 5/2016 |
| CA | 2963472 C | 5/2016 |
| CA | 3 023 675 A1 | 11/2017 |
| EP | 2 379 537 B1 | 10/2012 |
| EP | 2 379 537 B9 | 10/2012 |
| EP | 3 218 368 B1 | 12/2018 |
| WO | WO 2010/070068 A2 | 6/2010 |
| WO | WO 2016/077158 A1 | 5/2016 |
| WO | WO 2022/226660 A1 | 11/2022 |
| WO | WO 2023/018806 A1 | 2/2023 |

OTHER PUBLICATIONS

International Search Report for PCT/CA2024/051211, mailed Oct. 21, 2024, 4 pages.
Written Opinion of the International Search Authority for PCT/CA2024/051211, mailed Oct. 21, 2024, 5 pages.
Aas et al., "Feed Intake in Atlantic Salmon Fed with or without Surface Spreading of Feed," Journal of Agriculture and Marine Sciences, 25(1): 20-26 (2020).
Bravecto™, 1-month, (fluralaner) Chews for Dogs, Merck Animal Health (2020), 2 pages.
Credelio™ lotilaner for dogs, Elanco™, 1 page.
Credelio for cats, Elanco France S.A.S., 2 pages.
Search Report for European Application No. 24200357.2-1109, dated Jan. 30, 2025 (9 pages).
González-Morales et al., "Pharmacokinetics of fluralaner as a systemic drug to control infestations of the common bed bug, *Cimex lectularius*, in poultry facilities," Parasites & Vectors, 16:333 (2023), 8 pages.
NexGard® (afoxolaner) Chewables, Frontline Vet Labs™, a Division of Boehringer Ingelheim Animal Health USA Inc. (2020), 1 page.
Simparica® (sarolaner) Chewables, Zoetis (2024), 1 page.
UK Search and Examination Report for Application No. GB2413510.5, dated Dec. 23, 2024, 7 pages.

* cited by examiner

COMPOSITIONS AND METHODS OF A DIHYDROISOXAZOLE COMPOUND THAT REDUCES ECTOPARASITE INFESTATIONS ON FISH

CROSS-REFERENCE TO RELATED APPLICATIONS

The present application claims the benefit of U.S. provisional patent application Ser. No. 63/538,786 filed on Sep. 15, 2023 and U.S. provisional patent application Ser. No. 63/610,853 filed on Dec. 15, 2023. The contents of each of the above-referenced document are incorporated herein by reference in their entirety.

TECHNICAL FIELD

This application generally relates to the field of ectoparasite treatment on fish and, more specifically, to the use of an isoxazoline compound for treatment of ectoparasite infestations on fish, especially farmed fish.

BACKGROUND

Ectoparasite infestations in fish farming can pose significant challenges and issues for aquaculture operations. Ectoparasites are external parasites that associate themselves with the skin, gills, or fins of fish, feeding on their blood, mucus, or tissues. The most common ectoparasites in fish farming include parasitic copepods such as members of the genera *Lepeophtheirus*, *Caligus* and *Argulus* among others. Some of the key issues associated with ectoparasite infestations in fish farming may include reduced growth and feed conversion efficiency, skin and gill damage, secondary infections resulting from open wounds and, mortality associated with severe infestations. The economic impact of ectoparasite infestations can be significant for fish farmers, where for instance, mortality, reduced growth rates, and the cost of treatments can lead to significant economic losses.

Sea lice infestations are particularly challenging for aquaculture operations, in particular for salmonid aquaculture, where these crustacean ectoparasites feed on the mucus, tissues and blood of host marine fish. Sea lice belong to the class Copepoda, order Siphonostomatoida, family Caligidae and several genera including *Lepeophtheirus* and *Caligus*.

Since the beginning of large-scale farming of salmonid species, treatment or control of ectoparasites (such as sea lice) has been mainly based on chemotherapeutants administered in immersion baths or in medicated feed. Emamectin benzoate, or SLICE® (Merck Animal Health, USA), has been the most successful in-feed medicinal substance for sea lice control since it was introduced in 2000 and subsequently licensed in Canada, Norway, Scotland, Ireland, Faroe Islands and Chile. Emamectin benzoate is formulated in a premix which is prescribed by a veterinarian and sent to an aquaculture feed mill for top coating onto fish feed. However, due to the repeated and sometimes exclusive use of SLICE®, sea lice gradually developed resistance to this chemotherapeutant. Similarly, resistance to hydrogen peroxide has also been developing due to heavy reliance on its use in immersion treatments. Chemotherapeutant use is declining because of resistance issues, but the total frequency of treatment events continues to rise amidst ongoing ectoparasite (such as sea lice) infestation pressure, resulting in a significant increase in non-medicinal treatments.

Mechanical delousing systems are also commonly used in major salmonid farming regions. Mechanical delousing systems include high-pressure water jets and warm-water systems to detach sea lice. The stocking of cleaner fish in net pens has become a common practice in Europe and more recently, eastern Canada. However, this comes with additional welfare considerations for the care of cleaner fish, as well as the need to vaccinate them as per biosecurity measures, to prevent transmissible disease outbreaks in the salmon.

For the foreseeable future, ectoparasite infestations will continue to be a serious biological and economic problem for the fish farming industry, especially the Salmonidae farming industry. Ectoparasites such as sea lice have a significant capacity to quickly adapt to changes in the marine environment, enabling them to thrive under fish farming conditions despite human interventions.

Another challenge is that any therapeutant that targets ectoparasites such as sea lice may also have unintended secondary effects on other crustaceans that may be commercially important, such as lobsters, crabs, etc. The present disclosure seeks to address these outstanding problems.

U.S. Pat. No. 9,920,037 discloses a member of the isoxazoline benzamides (IOB) class, namely: (S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, including salts or solvates thereof, of structural formula

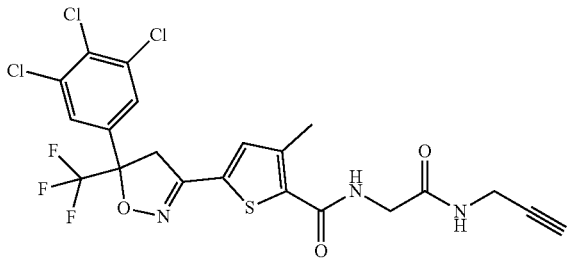 [SMILES: C#CCNC(=O)CNC(=O)c1sc(C2=NOC(c3cc(Cl)c(Cl)c(Cl)c3)(C(F)(F)F)C2)cc1C]

No market authorisation has been granted for this specific active ingredient for any species or indication. U.S. Pat. No. 9,920,037 discloses the use of the afore-mentioned compound for the reduction or elimination of ectoparasites in or on non-human animals, production livestock, companion animals and fish. U.S. Pat. No. 9,920,037 discloses that a dose of 1.0 mg/kg/d of the compound administered in medicated feed to Atlantic salmon for 7 consecutive days showed 100% efficacy against chalimus and pre-adult/adult stages of the sea louse, *Lepeophtherius salmonis*, when lice were counted on the fish 10 days after the end of treatment.

SUMMARY

This Summary is provided to introduce a selection of concepts in a simplified form that are further described below in the Detailed Description. This Summary is not intended to identify key aspects or essential aspects of the claimed subject matter.

The following non-limiting embodiments for this disclosure are envisioned:
1. A composition comprising active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, a salt, an N-oxide, or a solvate thereof, of structural formula

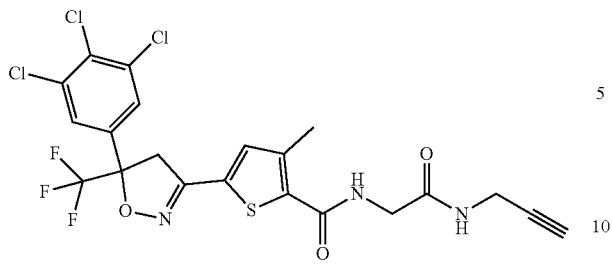
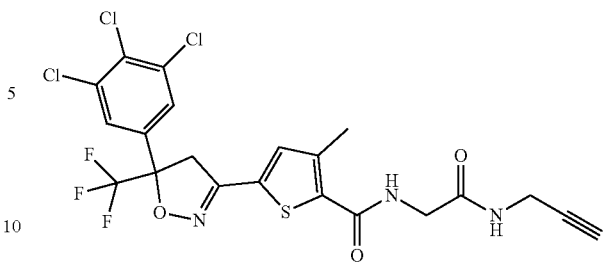

for oral administration in a dosage of from about 0.025 mg/kg/d to about 0.250 mg/kg/d, preferably of from about 0.025 mg/kg/d to about 0.125 mg/kg/d of the active ingredient, or salt, or N-oxide, or solvate thereof.

2. The composition according to embodiment 1, wherein the composition is prepared for feeding to fish at a feed rate within the range of from 0.4%-2.6% body weight/day.

3. The composition according to embodiment 1 or 2, wherein the oral administration is from about 3 to about 10 consecutive days, preferably during 7 consecutive days.

4. The composition according to any one of embodiments 1 to 3, comprising from about 0.01 wt. % to about 99 wt. %, preferably from about 0.01 wt. % to about 0.5 wt. %, more preferably from about 0.1 wt. % to about 0.5 wt. % of the active ingredient, or salt, or N-oxide, or solvate thereof.

5. The composition according to any one of embodiments 1 to 4, wherein the composition is a medicated fish feed.

6. The composition according to embodiment 5, wherein the medicated fish feed is a feed pellet or feed granule.

7. The composition according to any one of embodiments 1 to 6, wherein the dosage is of about 0.025 mg/kg/d, about 0.050 mg/kg/d, or about 0.125 mg/kg/d.

8. The composition according to any one of embodiments 1 to 7, wherein the composition is prepared for oral administration to fish.

9. The composition according to embodiment 8, wherein the fish is a salmonid.

10. The composition according to any one of embodiments 1 to 9, wherein the composition is prepared for treatment or control of an ectoparasite infestation on the fish.

11. The composition according to embodiment 10, wherein the ectoparasite infestation is a sea lice infestation. For example, the sea lice infestation involves copepodids, chalimi, pre-adults, or adults, or a combination of lice life stages in infestations.

12. A composition comprising active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, or a salt, or an N-oxide, or a solvate thereof, of structural formula for use in treatment or control of an ectoparasite infestation on fish, wherein the composition is for oral administration to the fish in a dosage of from about 0.025 mg/kg/d to about 0.250 mg/kg/d, preferably of from about 0.025 mg/kg/d to about 0.125 mg/kg/d of the active ingredient, or salt, or N-oxide, or solvate thereof.

13. The composition for the use according to embodiment 12, wherein the fish is a salmonid.

14. The composition for the use according to embodiment 12 or 13, wherein the ectoparasite infestation is a sea lice infestation. For example, the sea lice infestation involves copepodids, chalimi, pre-adults, or adults, or a combination of lice life stages in infestations.

15. The composition for the use according to any one of embodiments 12 to 14, wherein the composition comprises from about 0.01 wt. % to about 99 wt. %, preferably from about 0.01 wt. % to about 0.5 wt. %, more preferably from about 0.1 wt. % to about 0.5 wt. % of the active ingredient, or salt, or N-oxide, or solvate thereof.

16. The composition for the use according to any one of embodiments 12 to 15, wherein the composition is a medicated fish feed.

17. The composition for the use according to embodiment 16, wherein the medicated fish feed is in the form of a feed pellet or feed granule.

18. The composition for the use according to any one of embodiments 12 to 17, wherein the composition is prepared for feeding to the fish at a feed rate within the range of from 0.4%-2.6% body weight/day.

19. The composition for the use according to any one of embodiments 12 to 18, wherein the dosage is of about 0.025 mg/kg/d, about 0.050 mg/kg/d or about 0.125 mg/kg/d.

20. The composition for the use according to any one of embodiments 12 to 19, wherein the composition is for oral administration during from about 3 to about 10 consecutive days, preferably during 7 consecutive days.

21. A method for treatment or control of an ectoparasite infestation on fish, comprising oral administration to the fish of active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl) thiophene-2-carboxamide, or salt, or N-oxide, or solvate thereof, of structural formula

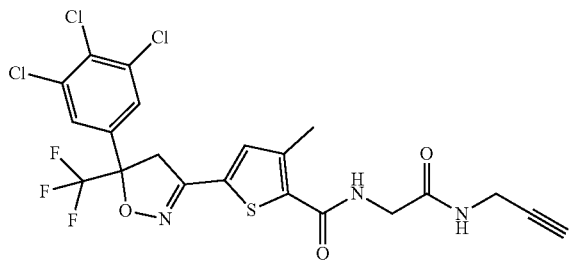 [SMILES: C#CCNC(=O)CNC(=O)c1sc(C2=NOC(c3cc(Cl)c(Cl)c(Cl)c3)(C(F)(F)F)C2)cc1C]

in a dosage of from about 0.025 mg/kg/d to about 0.250 mg/kg/d, preferably of from about 0.025 mg/kg/d to about 0.125 mg/kg/d.

22. The method according to embodiment 21, wherein the ectoparasite infestation is a sea lice infestation. For example, the sea lice infestation involves copepodids, chalimi, pre-adults, or adults, or a combination of lice life stages in infestations.

23. The method according to embodiment 21 or 22, wherein the oral administration is from about 3 to about 10 consecutive days, preferably during 7 consecutive days.

24. The method according to any one of embodiments 21 to 23, wherein the active ingredient, or salt, or N-oxide, or solvate thereof, is comprised in a fish oral composition.

25. The method according to embodiment 24, wherein the fish oral composition comprises from about 0.01 wt. % to about 99 wt. %, preferably from about 0.01 wt. % to about 0.5 wt. %, more preferably from about 0.1 wt. % to about 0.5 wt. % of the active ingredient, or salt, or N-oxide, or solvate thereof.

26. The method according to embodiment 24 or 25, wherein the fish oral composition is a fish feed.

27. The method according to embodiment 26, wherein the fish feed is a feed pellet or feed granule.

28. The method according to any one of embodiments 21 to 27, wherein the dosage is of about 0.025 mg/kg/d, about 0.050 mg/kg/d, or about 0.125 mg/kg/d of the active ingredient, or salt, or N-oxide or solvate thereof.

29. The method according to any one of embodiments 21 to 28, wherein the fish is a salmonid.

30. Use of active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, or a salt, or an N-oxide, or a solvate thereof, of structural formula

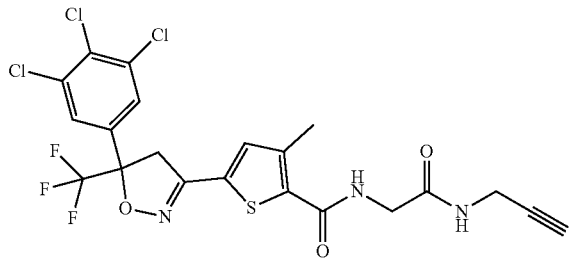 [SMILES: C#CCNC(=O)CNC(=O)c1sc(C2=NOC(c3cc(Cl)c(Cl)c(Cl)c3)(C(F)(F)F)C2)cc1C]

in the manufacture of a composition for use in treatment or control of an ectoparasite infestation on fish, wherein the composition is for oral administration to the fish in a dosage of from about 0.025 mg/kg/d to about 0.250 mg/kg/d, preferably of from about 0.025 mg/kg/d to about 0.125 mg/kg/d of the active ingredient, or salt, or N-oxide, or solvate thereof.

31. The use according to embodiment 30, wherein the ectoparasite infestation is a sea lice infestation. For example, the sea lice infestation involves copepodids, chalimi, pre-adults, or adults, or a combination of lice life stages in infestations.

32. The use according to embodiment 30 or 31, wherein the oral administration is from about 3 to about 10 consecutive days, preferably during 7 consecutive days.

33. The use according to any one of embodiments 30 to 32, wherein the composition is a fish oral composition.

34. The use according to embodiment 33, wherein the fish oral composition comprises from about 0.01 wt. % to about 99 wt. %, preferably from about 0.01 wt. % to about 0.5 wt. %, more preferably from about 0.1 wt. % to about 0.5 wt. % of the active ingredient, or salt, or N-oxide, or solvate thereof.

35. The use according to embodiment 33 or 34, wherein the fish oral composition is a fish feed.

36. The use according to embodiment 35, wherein the fish feed is a feed pellet or feed granule.

37. The use according to any one of embodiments 30 to 36, wherein the dosage is of about 0.025 mg/kg/d, about 0.050 mg/kg/d, or about 0.125 mg/kg/d.

38. The use according to any one of embodiments 30 to 37, wherein the fish is a salmonid.

39. The composition for the use according to any one of embodiments 12 to 20, wherein the composition is for feeding to the fish at a feed rate within the range of from 0.4%-2.6% body weight/day.

All features of exemplary embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

BRIEF DESCRIPTION OF THE SEVERAL VIEWS OF THE DRAWINGS

A detailed description of specific exemplary embodiments is provided herein below with reference to the accompanying drawings in which.

Figure 1:
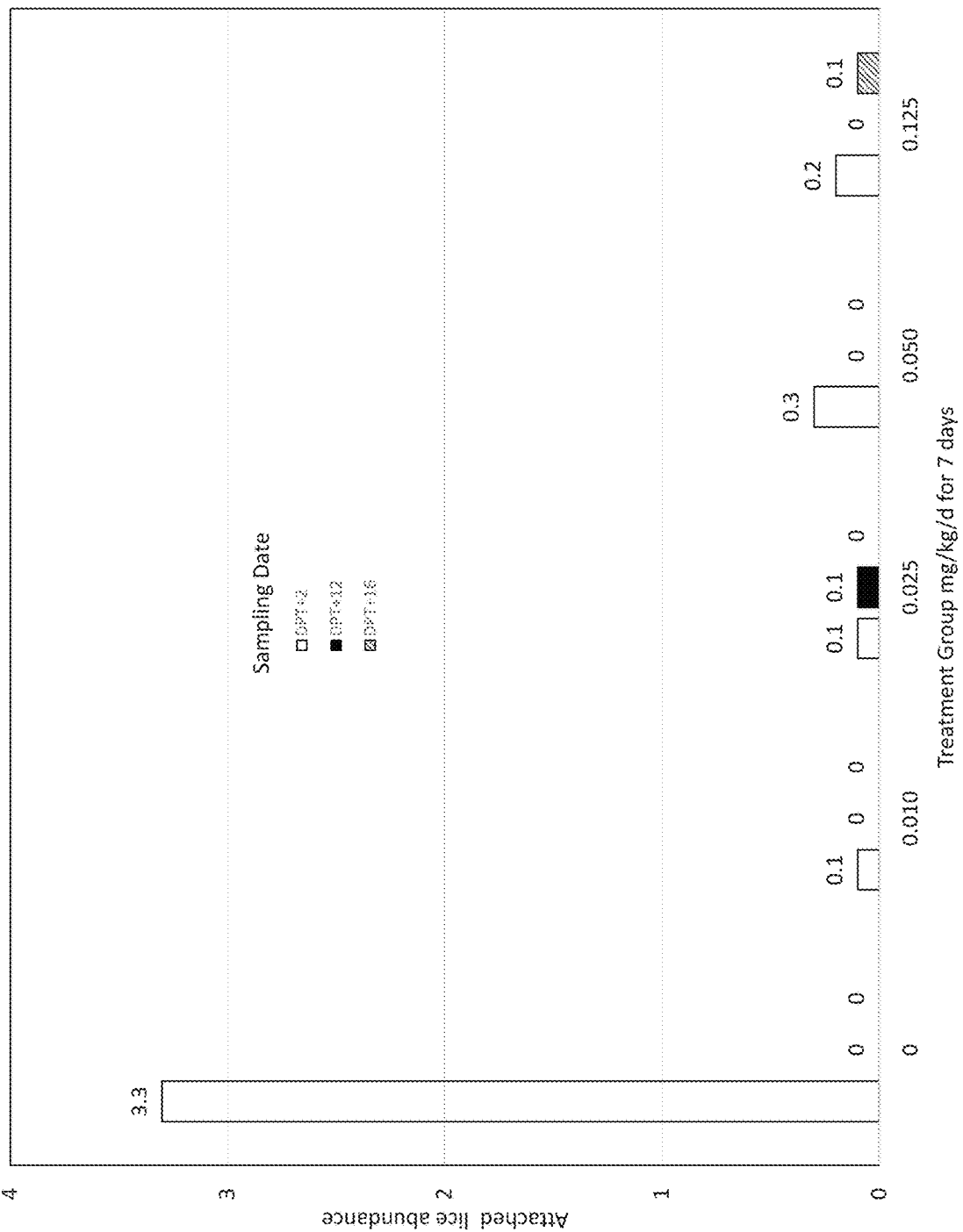
FIG. 1 is a non-limiting chart showing the mean number of attached lice (chalimus stages 1 & 2)/fish when fish were infested with sea lice 17 days before administration of dose rates of: 0 (negative control), 0.010, 0.025, 0.050 and 0.125 mg/kg/d, respectively, for 7 consecutive days. Lice were counted at 2, 12, and 16 days post-treatment (DPT).
Figure 2:
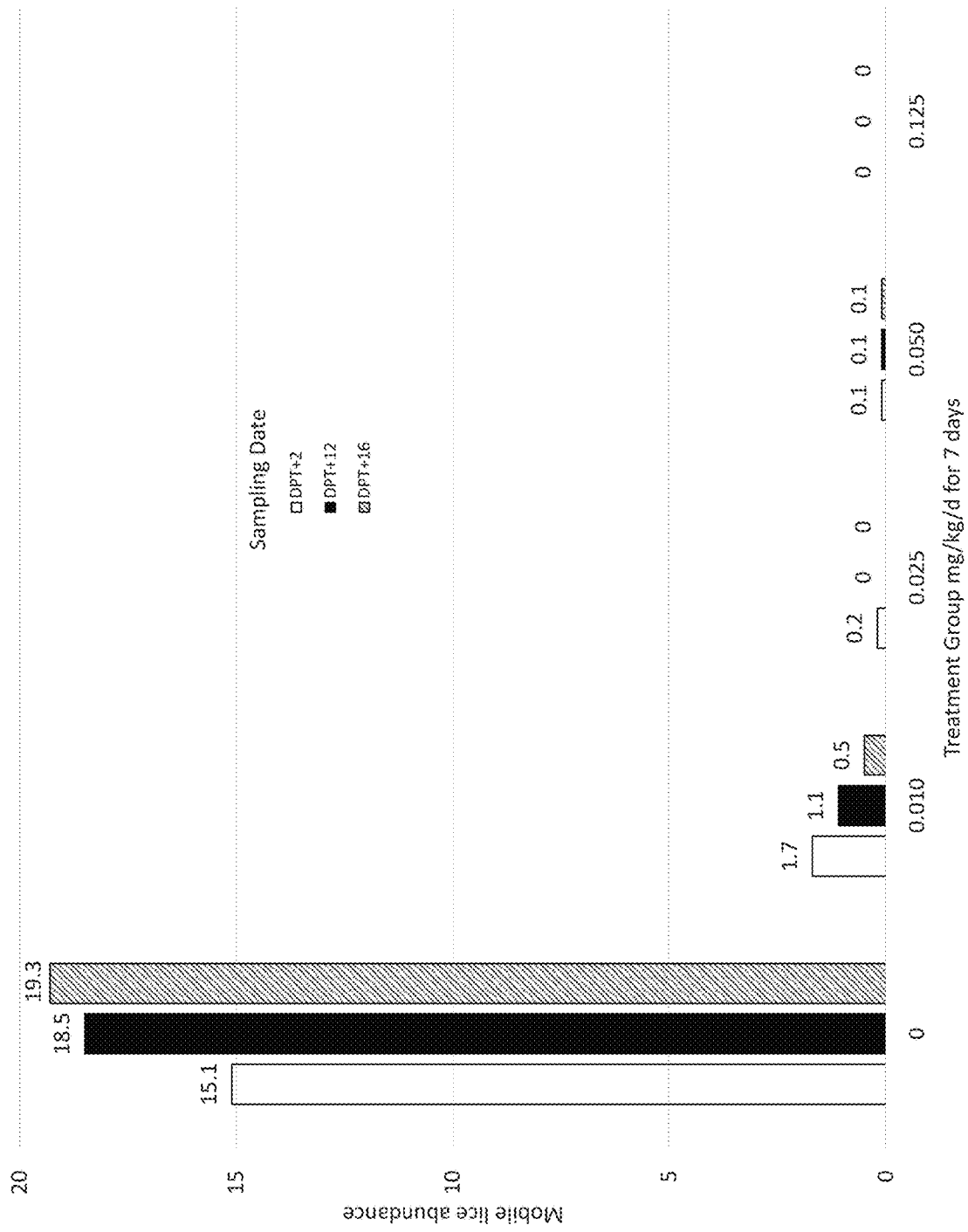
FIG. 2 is a non-limiting chart showing the mean number of mobile lice (pre-adult & adult lice)/fish when fish were infested with sea lice 17 days before administration of dose rates of 0 (negative control), 0.010, 0.025, 0.050 and 0.125 mg/kg/d, respectively, for 7 consecutive days. Lice were counted at 2, 12, and 16 DPT.
Figure 3:
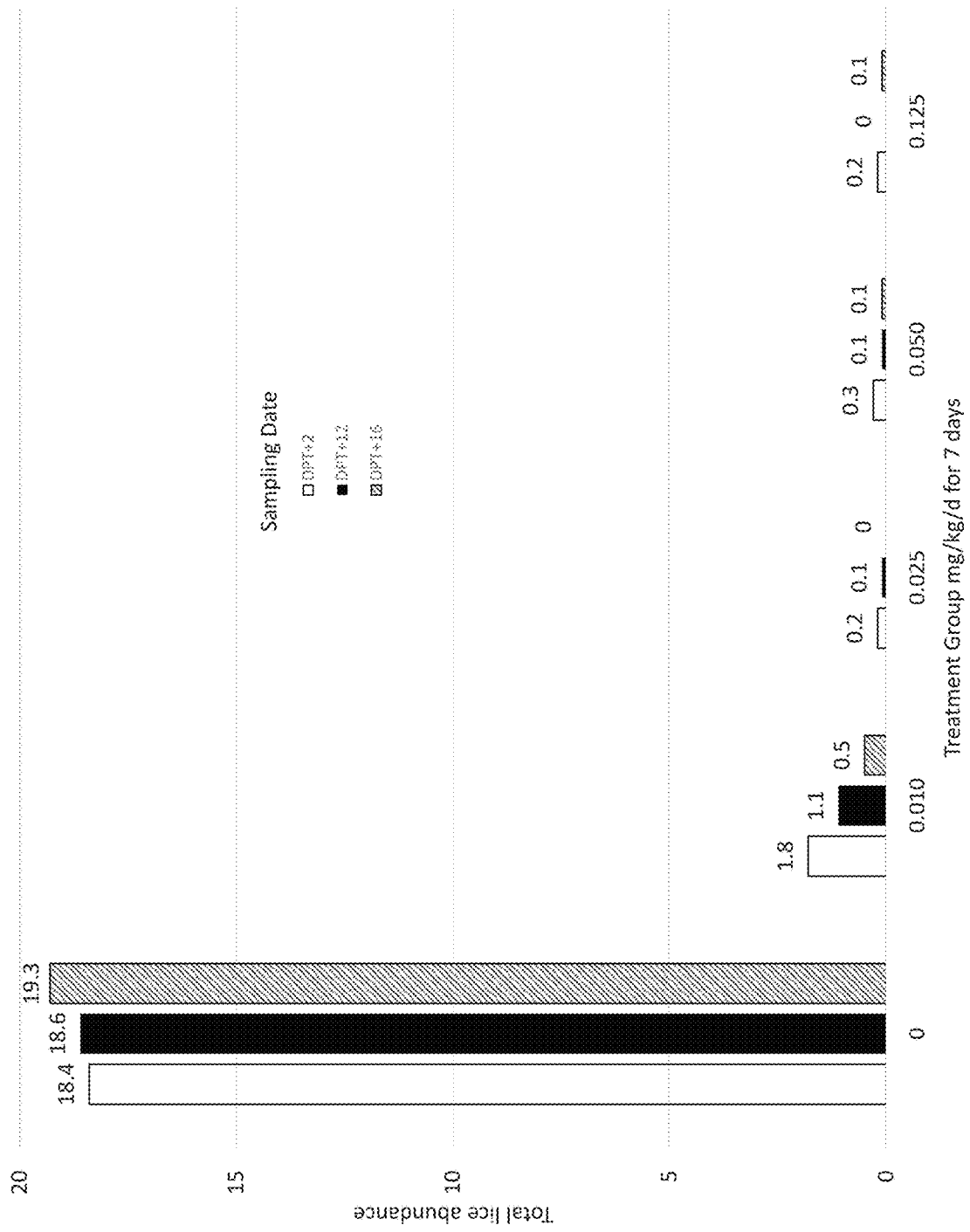
FIG. 3 is a non-limiting chart showing the mean total number of sea lice/fish when fish were infested with sea lice 17 days before administration of dose rates of either 0 (negative control), 0.010, 0.025 0.050 or 0.125 mg/kg/d, respectively, for 7 consecutive days. Lice were counted at 2, 12, and 16 DPT.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art considering the instant disclosure in which variations and additions do not depart from the present technology. Hence, the following description is intended to illustrate some embodiments of the technology, and not to exhaustively specify all permutations, combinations, and variations thereof.

The present inventors have surprisingly and unexpectedly discovered that oral administration of the active ingredient (S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide (also referred to in this text as "S-roxapin"), including salts, N-oxides, or solvates thereof, of structural formula

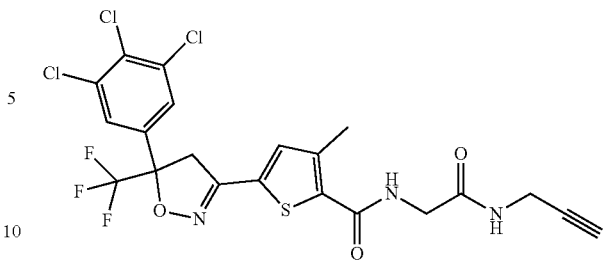

is therapeutically active against an ectoparasite infestation (such as sea lice) on fish (such as members of the Salmonidae) in a dosage (i.e., in a dose rate) of from about 0.025 mg/kg/d to about 0.250 mg/kg/d, preferably in a dosage of from about 0.025 mg/kg/d to about 0.125 mg/kg/d, i.e., up to 40-fold dosage reduction compared to the dosage proposed in U.S. Pat. No. 9,920,037. Throughout this specification, the expression "mg/kg/d" means administration of milligrams of the active ingredient, or salt, or N-oxide, or solvate thereof per kilogram of fish bodyweight and per day. Throughout this specification, the expression "at a dosage" or "in a dose rate" or "in a dosage regime" can be interchangeably used.

In some embodiments, the active ingredient, or salt, or N-oxide, or solvate thereof, is administered over a period of from about 3 to about 10 consecutive days, preferably over a period of at least 7 consecutive days, more preferably a period of 7 consecutive days.

An at least 7 consecutive day treatment is preferable because of a well-documented feeding hierarchy among fish. Therefore, this is remedied by at least a 7 consecutive day treatment, which allows for a more uniform feed uptake among the population.

Such reduced dosage affords a technical advantage in commercial fish aquaculture settings due to the resulting reduced likelihood of negative environmental effects, e.g., adverse effects on non-target species. In other words, the herein described reduced dosage of the active ingredient, or salt or N-oxide or solvate thereof, for control or treatment of an ectoparasite infestation (such as sea lice) on a fish (such as salmonids) reduces the release thereof to the aquatic environment in proximity to the fish farms, which may, otherwise, negatively impact other aquatic organisms.

Without being bound by any theory, it is believed that such therapeutic activity at the herein described reduced dosage was unexpected and not foreseeable. The active ingredient(S)-3-methyl-N-(2-oxo-2-(prop-2-yn-1-ylamino) ethyl)-5-(5-(3,4,5-trichlorophenyl)-5-(trifluoromethyl)-4,5-dihydroisoxazol-3-yl)thiophene-2-carboxamide, or salt, or N-oxide, or solvate thereof, is a member of the isoxazoline benzamide (IOB) class. Its putative pharmacological properties were inferred from its structure and the known effects of related compounds in its class, but the dose had to be derived empirically, with unpredictable dose effects. Drug metabolism in fish, including salmonids, is temperature dependent, unlike homoeothermic animals (mammals or birds), and specific metabolic pathways for clearance of drug compounds are poorly understood. No market authorization has been granted for this specific active ingredient, or salt or N-oxide, or solvate thereof, for any species or indication. There are no published data available for its intended indication (treatment of ectoparasites such as sea lice) in the intended target species (fish, such as Salmonidae) at these low dose rates.

Four members of the IOB class are on the market for flea and tick prevention in dogs and cats globally, i.e., afoxolaner (NexGard™), sarolaner (Simparica™), lotilaner (Credelio™) and fluralaner (Bravecto™). Fluralaner (Bravecto™) is approved in a food animal species in Europe against red mites on poultry at a dose rate of 0.5 mg/kg bw (bodyweight of the animal) administered twice in drinking water 7 days apart for a total dose of 1.0 mg/kg bw. Dose rates for the above-mentioned members of the IOB class in dogs and cats are higher, ranging from 2-40 mg/kg bw (bodyweight of the animal) administered in a single oral dose per treatment.

While compounds in this class act with similar modes of action (in this case on the gamma-aminobutyric acid (GABA) and glutamate gated chloride channels), differences do exist among them that influence pharmacological activity. For example, a closely related compound to the disclosed compound shown below, was shown to be inactive against the copepodid stage of sea lice in a bath at similar dosage.

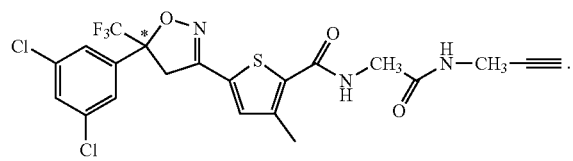 [SMILES: C#CCNC(=O)CNC(=O)c1sc(C2=NOC(c3cc(Cl)cc(Cl)c3)(C(F)(F)F)C2)cc1C ; "."]

The above compound only differs slightly from the disclosed compound, demonstrating how seemingly even the smallest of atomical differences can affect pharmacological activity.

More generally, labeled doses among the four approved drugs range from 0.5 mg/kg administered twice in drinking water 7 days apart for a total dose of 1.0 mg/kg per treatment (poultry) to 2-40 mg/kg administered in a single oral dose per treatment to dogs and cats.

The inventors conducted a first set of experiments with administration in medicated feed over 7 consecutive days to salmon of 0.050, 0.125, 0.250 mg/kg/d to determine a non-therapeutic dosage for control or treatment of sea lice infestation. As these lower dosages represented a large reduction in concentration to that described in U.S. Pat. No. 9,920,037 (1.0 mg/kg/d) and, as well, represented concentrations well below the dosage for related IOB products for dogs, cats and poultry approved between 2014 and 2021 by such regulatory authorities as the U.S. Food and Drug Administration, Health Canada, and the European Medicines Agency, it was reasonable to expect to find a non-therapeutic dosage at the lower dosages tested. Surprisingly, all dose rates evaluated in this first set of experiments were nearly 100% effective in reducing sea lice burdens.

Figure 4:
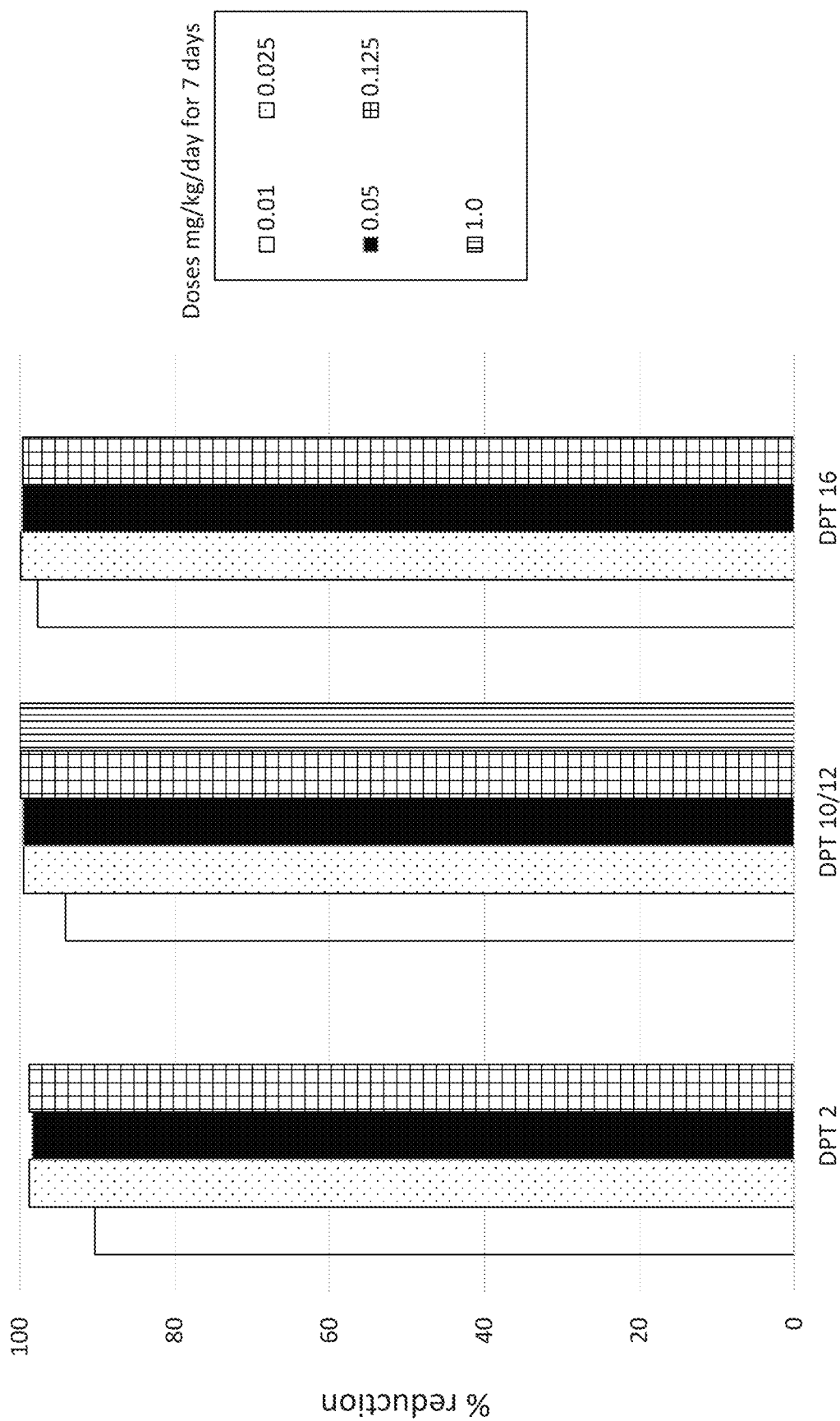
FIG. 4 is a non-limiting chart showing the percent (%) reduction in total number of sea lice/fish relative to an untreated control when fish were infested with sea lice before administration of dose rates of 0.010, 0.025, 0.050, 0.125, and 1.0 mg/kg/d, for 7 consecutive days, respectively. Lice were counted at 10 DPT for the 1.0 mg/kg/d doses and at 2, 12, and 16 DPT for the 0.010, 0.025, 0.050, and 0.125 mg/kg/d doses.
Figure 5:
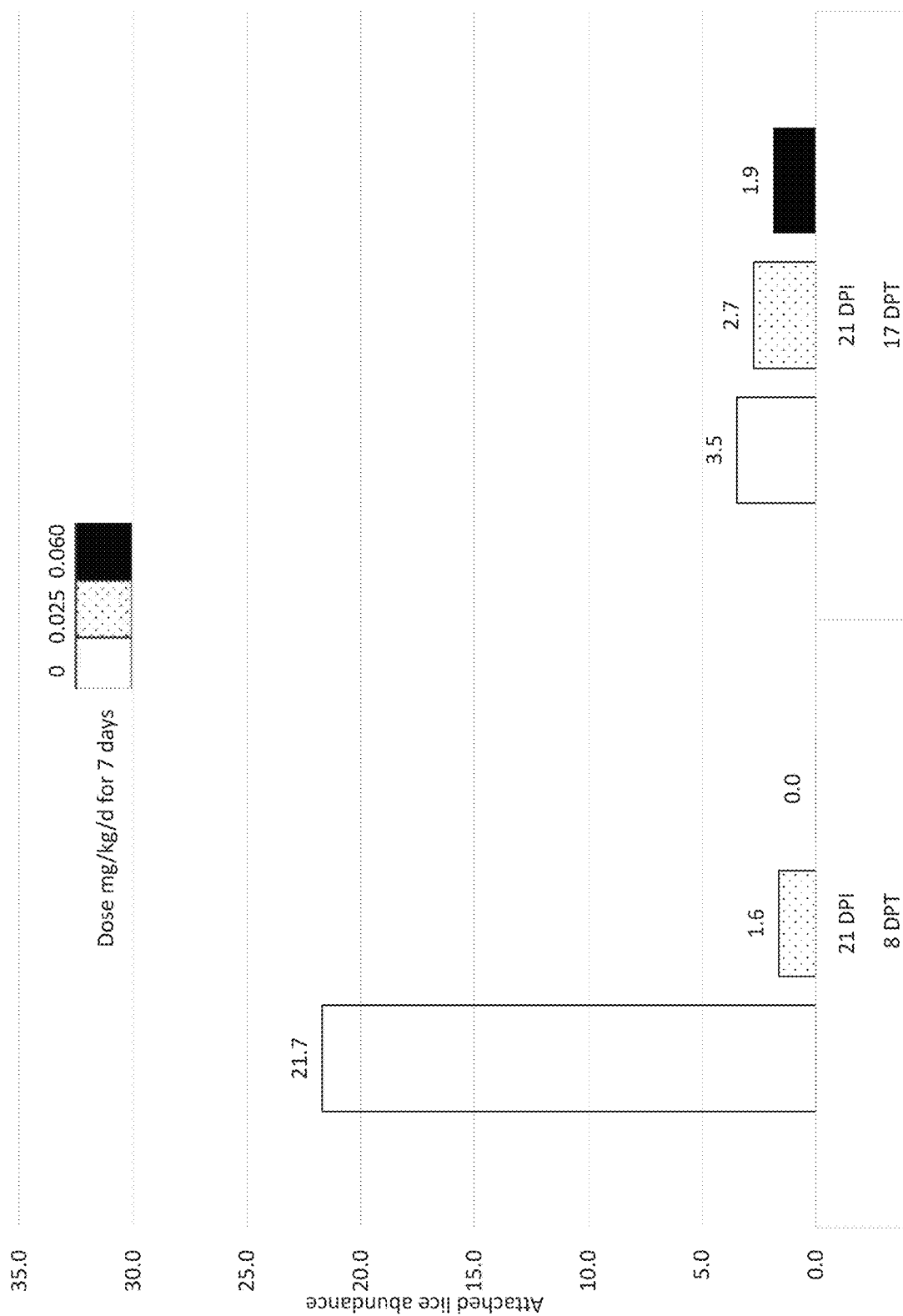
FIG. 5 is a non-limiting chart showing the mean number of attached lice (chalimus stages 1 & 2)/fish following administration of dose rates of 0 (negative control), 0.025 and 0.060 mg/kg/d respectively for 7 consecutive days and infestation at 8 and 17 DPT. Lice were counted at 21-days post infestation (DPI).
Figure 6:
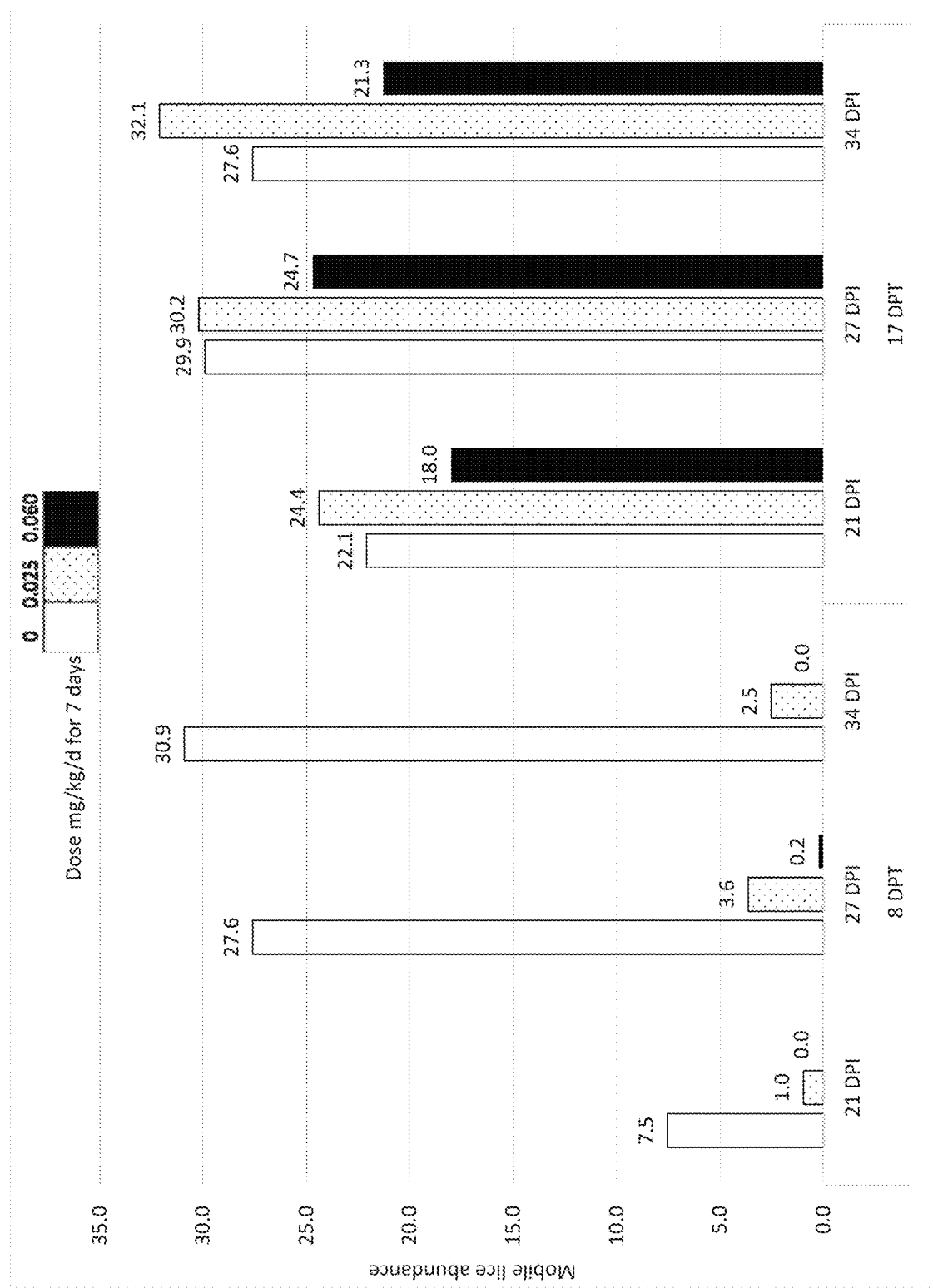
FIG. 6 is a non-limiting chart showing the mean number of mobile lice (pre-adult & adult lice)/fish following administration of dose rates of 0 (negative control), 0.025 and 0.060 mg/kg/d respectively for 7 consecutive days and infestation at 8 and 17 DPT. Lice were counted at 21, 27 and 34 DPI.
Figure 7:
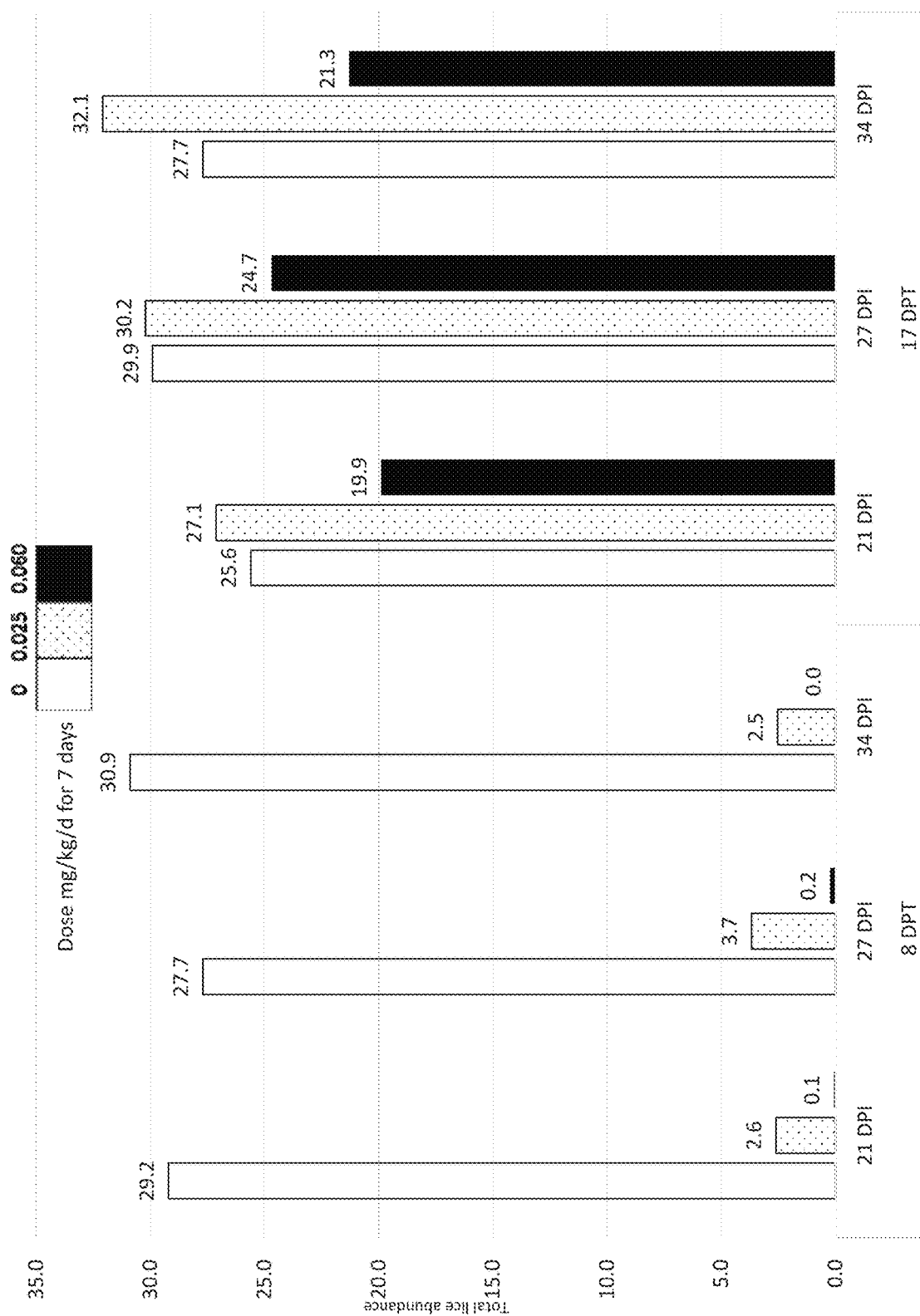
FIG. 7 is a non-limiting chart showing the mean total number of sea lice/fish following administration of dose rates of 0 (negative control), 0.025 and 0.060 mg/kg/d respectively for 7 consecutive days and infestation at 8 and 17 DPT. Lice were counted at 21, 27 and 34 DPI.
Figure 8:
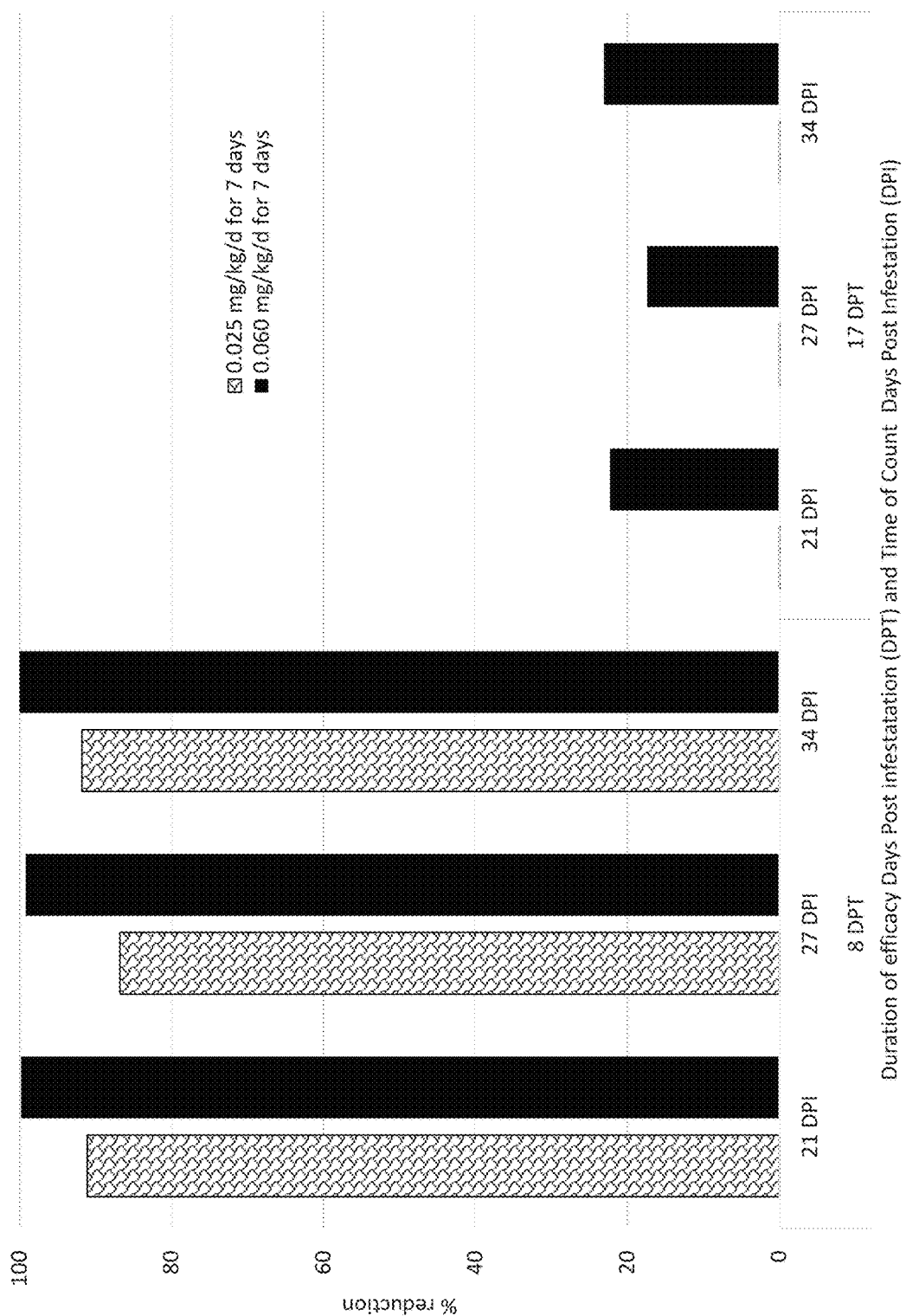
FIG. 8 is a non-limiting chart showing the percent (%) reduction in total number of sea lice/fish relative to untreated control following administration of dose rates of 0 (negative control), 0.025 and 0.060 mg/kg/d respectively for 7 consecutive days and infestation at 8 and 17 days post treatment. Lice were counted at 21, 27 and 34 DPI.

The inventors then conducted a second set of experiments with administration in medicated feed over 7 consecutive days to salmon at still lower dosages of 0.010, 0.025, 0.050 and 0.125 mg/kg/d to find a non-therapeutic dosage for control or treatment of sea lice infestation. Results indicated that the dosages of 0.025, 0.050 and 0.125 mg/kg/d had significantly higher efficacy than the lowest dosage (0.010 mg/kg/d). This difference suggested the first approximation of a non-therapeutic dosage. It was provisionally concluded that the observed minimum efficacious dosage was in the range of 20-40 times lower than shown in U.S. Pat. No. 9,920,037. There was no way of reasonably predicting that it would continue to be efficacious at 20-40 times lower concentrations than shown in U.S. Pat. No. 9,920,037. These results are depicted in FIG. 4, which shows a % reduction of sea lice for dosages at 0.025, 0.050 and 0.125 mg/kg/d similar to that observed for the 1.0 mg/kg/d dosage described in U.S. Pat. No. 9,920,037.

In some embodiments, the present disclosure relates to a composition comprising active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl) thiophene-2-carboxamide, or salt, or N-oxide, or solvate thereof, of structural formula

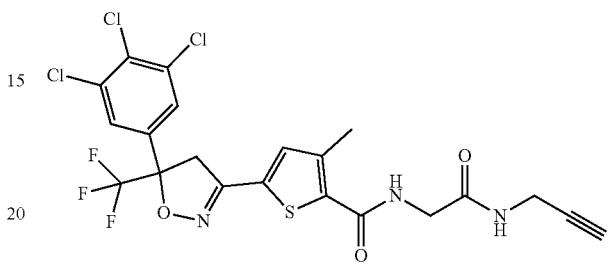

for oral administration in a dosage of from about 0.025 mg/kg/d to about 0.250 mg/kg/d, preferably of from about 0.025 mg/kg/day to about 0.125 mg/kg/d of the active ingredient, or salt, or N-oxide or solvate thereof.

In some embodiments, the present disclosure relates to a composition comprising active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl) thiophene-2-carboxamide, or salt, or N-oxide, or solvate thereof, of structural formula,

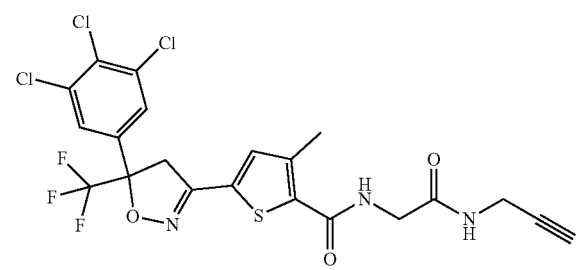 [SMILES: C#CCNC(=O)CNC(=O)c1sc(C2=NOC(c3cc(Cl)c(Cl)c(Cl)c3)(C(F)(F)F)C2)cc1C]

for use in treatment of an ectoparasite infestation (such as sea lice) on fish (such as salmonids), wherein the composition is for oral administration to the fish in a dosage of from about 0.025 mg/kg/d to about 0.250 mg/kg/d, preferably of from about 0.025 mg/kg/d to about 0.125 mg/kg/d of the active ingredient, or salt, or N-oxide, or solvate thereof.

In some embodiments, the present disclosure relates to a method for treatment of an ectoparasite infestation on fish, comprising oral administration of active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, or salts, or N-oxide, or solvates thereof, of structural formula

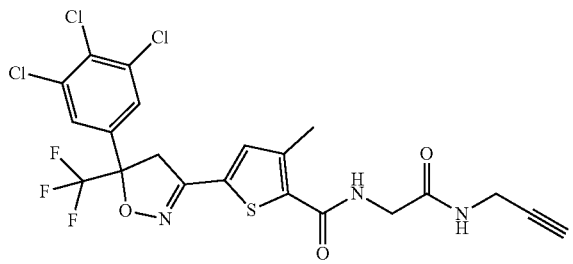 [SMILES: C#CCNC(=O)CNC(=O)c1sc(C2=NOC(c3cc(Cl)c(Cl)c(Cl)c3)(C(F)(F)F)C2)cc1C]

in a dosage of from about 0.025 mg/kg/day to about 0.250 mg/kg/day, preferably from about 0.025 mg/kg/day to about 0.125 mg/kg/day.

In some embodiments, the present disclosure relates to a use of active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, or a salt, or an N-oxide, or a solvate thereof, of structural formula

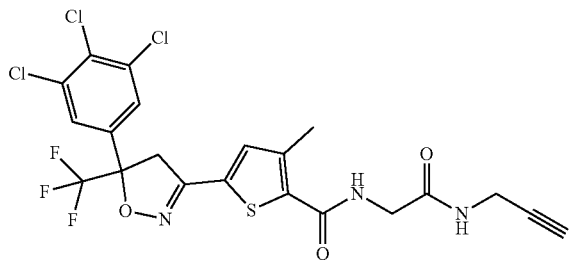 [SMILES: C#CCNC(=O)CNC(=O)c1sc(C2=NOC(c3cc(Cl)c(Cl)c(Cl)c3)(C(F)(F)F)C2)cc1C]

in the manufacture of a composition for use in treatment or control of an ectoparasite infestation on fish, wherein the composition is for oral administration to the fish in a dosage of from about 0.025 mg/kg/d to about 0.250 mg/kg/d, preferably of from about 0.025 mg/kg/d to about 0.125 mg/kg/d of the active ingredient, or salt, or N-oxide, or solvate thereof.

In some embodiments, the composition described herein will be recognized by those skilled in the art to include, for example, such forms as liquid formulation or solid forms. For example, solid forms may include capsules, powders including soluble powders, granules, pellets, or embedding of the active ingredient, or salt, or N-oxide, or solvate thereof, in polymeric substances, like cross-linked alginate particles. Liquid forms may include ready-to-use liquids or powders of the active ingredient, or salt, or N-oxide, or solvate thereof, for reconstitution, which may be administered by oral and parenteral (injectable, immersion, and topical) routes.

In some embodiments, for ease of administration, the composition may include medicated fish feed, e.g., fish feed which has been supplemented to include the herein described active ingredient, or salt, or N-oxide, or solvate thereof. Such fish feed is typically prepared by commercial feed mills according to the instructions of a veterinarian (e.g., a prescription) and/or based on the label, and shipped to the fish farm. For example, in some jurisdictions, such commercial feed mills can be regulated and "licensed" by local regulatory authorities to allow them to manufacture medicated fish feed. Alternatively, such medicated feed can be prepared at the fish farm where permitted.

In some embodiments, the fish feed described herein may take the form of feed pellets or granules. Fish feed is commonly presented in granular or pellet forms, comprising components such as fishmeal, fish oil, vegetable proteins, poultry meal, feather meal, pork protein meal, saccharides, and polysaccharides (such as mannans, glucans, and alginates). Additionally, formulations may include excipients like pigments, vitamins, minerals, and binders. The active component, salt, N-oxide, or solvate thereof, can be integrated into the feed pre-pelleting. Alternatively, the active ingredient, salt, N-oxide, or solvate thereof, may be applied as a coating onto the feed granules or pellets, either independently or within a premix. This premix, along with the active component, salt, N-oxide, or solvate thereof, may encompass acceptable veterinary excipients like starch, fumed silica, microcrystalline cellulose, lactose, and a preservative. Incorporation of the active ingredient, salt, N-oxide, or solvate into the feed mixture can occur prior to the pelleting process. Fish feed, such as salmonid feeds are known in the art and will not be further described here, for conciseness sake.

In some embodiments, the complete treatment duration for administering the active ingredient, salt, N-oxide, or solvate to fish is of about 3 to about 14 consecutive days (about 2 weeks). In some embodiments, it ranges from about 3 to about 7 consecutive days, while in another embodiment, it extends from about 5 to about 14 consecutive days. In yet another embodiment, the treatment duration is from about 5 to about 10 consecutive days (about 1 and a half weeks). Preferably, the treatment duration is of at least 7 consecutive days. More preferably, the treatment duration is of 7 consecutive days.

In some embodiments, the composition includes fish feed that contains the herein described active ingredient, or salt, or N-oxide, or solvate thereof. For example, the active ingredient or salt, or N-oxide, or solvate thereof, may be incorporated into a premix that is incorporated into or coated onto fish feed. The premix can be applied to fish feed by dry mixing followed by application of an oil coating or by mixing the premix in oil that is sprayed onto the fish feed.

In some embodiments, when the fish feed includes the active ingredient, or salt, or N-oxide, or solvate thereof, on at least a surface portion thereof, the active ingredient, or salt, or N-oxide, or solvate thereof, may be coated with a suitable oil layer. The person of skill in the art will recognize that there are several commercially available and suitable oils for such purpose, for example, herring fish oil or vegetable oil.

As a general non-limiting rule, the composition described herein contains about 0.01 wt. % to about 99 wt. %, such as about 0.01 wt. % to about 95 wt. % of the active ingredient, or salt, or N-oxide, or solvate thereof. The reader will readily understand that the afore-mentioned ranges include any value therein, such as about 0.01 wt. % (about 0.1 mg/g), about 0.02 wt. % (about 0.2 mg/g), about 0.025 wt. % (about 0.25 mg/g), about 0.03 wt. % (about 0.30 mg/g), about 0.04 wt. % (about 0.40 mg/g), about 0.05 wt. % (about 0.50 mg/g), about 0.06 wt. % (about 0.60 mg/g), about 0.07 wt. % (about 0.70 mg/g), about 0.08 wt. % (about 0.80 mg/g), about 0.09 wt. % (about 0.90 mg/g), about 0.1 wt. % (about 1.0 mg/g), about 0.2 wt. % (about 2.0 mg/g), about 0.25 wt. % (about 2.5 mg/g), about 0.3 wt. % (about 3.0 mg/g), about 0.4 wt. % (about 4.0 mg/g), about 0.5 wt. % (about 5.0 mg/g), or more. The reader will also readily understand that the afore-mentioned values may form suitable ranges containing such values, such as from about 0.01 wt. % (about 0.1 mg/g) to about 0.5 wt. % (about 5.0 mg/g), or from about 0.1 wt. % (about 1.0 mg/g) to about 0.5 wt. % (about 5.0 mg/g). The reader will also readily understand that based on current industry practice, the medicated feed (i.e., the composition of the present disclosure) can be prepared for feeding to the fish at a feed rate within the range of from 0.4%-2.6% body weight/day ("bw/d"), including any values or ranges therein.

In some embodiments, the duration of efficacy obtained against sea lice on salmon with the herein described dosage is at least 90% efficacy, for example, for at least 2 days post-treatment, preferably for at least 12 days post-treatment, and may be expected for up to 16 days post-treatment.

In some embodiments, the active ingredient, or salt, or N-oxide, or solvate thereof is used to control or treat fish-parasitic crustaceans, particularly for addressing infestations of sea lice involving copepodids, chalimi, pre-adults, or adults, or a combination of lice life stages in infestations.

The term "fish" as used herein, unless otherwise indicated, refers to the taxonomic class Chondrichthyes (cartilaginous fishes, e.g., sharks and rays) and Osteichthyes (bony fishes) which live in water, have gills or mucus-covered skin for respiration, fins, and may have scales. This includes food fish, breeding fish and aquarium, pond fish, and farmed fish of all ages occurring in freshwater, seawater (e.g., marine) and brackish water. The present disclosure relates more particularly, to marine fish, and more particularly to marine food fish, especially salmon. Within the scope of this invention the term "salmon" will be understood as comprising all representatives of the family Salmonidae, especially, the following species: *Salmo salar* (Atlantic salmon); *Salmo trutta* (brown or sea trout); *Oncorhynchus mykiss* (rainbow trout); and the Pacific salmon (*Oncorhynchus*): *O. gorbuscha; O. keta; O. nerka; O. kisutch, O. tshawytscha* and *O. masou*; also comprised are artificially propagated species such as *Salvelinus* spp. and *Salmo clarki*. Preferred hosts of the present disclosure are Atlantic and Pacific salmon and sea trout.

Fish population means a group of individual fish that are kept in a confined area such as in seawater tanks, cages, or nets. Cages and nets are anchored in sea inlets, allowing a daily tidal water flow to pass through them, ensuring an ample supply of oxygen and clean water. Tanks, on the other hand, either maintain a continuous flow of seawater or undergo scheduled flushing with fresh seawater to guarantee optimal water quality and oxygen levels for maintaining fish health. In this controlled environment, fish are fed and, if needed, administered medication until they reach maturity for marketing as edible fish or are chosen for further breeding.

In one embodiment of the present disclosure, the active ingredient, or salt, or N-oxide, or solvate thereof, is administered to a fish population at the end of the freshwater stage or at the beginning of the seawater stage in the farming of the fish. According to another embodiment, the administration is performed whilst the fish (e.g., salmon or sea trout) are kept in seawater.

In accordance with the present disclosure, the active ingredient, or salt, or N-oxide, or solvate thereof is especially suited for use in the control or treatment of an ectoparasite infestation on fish, such as e.g., sea lice. The term "sea louse" designates a group of fish-parasitic crustaceans, specifically ectoparasitic copepods, that infest fish in seawater. In this context, "sea lice" refers to parasitic copepods within the order Siphonostomatoida, feeding on the mucus, skin, and tissues of their host. This category includes the families Caligidae and Lernanthropidae. Notably, two members of the Caligidae family, *Lepeophtheirus* spp. and *Caligus* spp. (C), lead to significant losses in salmonid fish farming. Examples of subspecies within *Lepeophtheirus* spp. (L) are *Lepeophtheirus salmonis oncorhynchi* subsp. nov and *L. salmonis salmonis*. Examples within *Caligus* spp. include *Caligus clemensi, Caligus curtus, Caligus dussumieri, Caligus elongatus, Caligus longicaudatus, Caligus rogercresseyi*, and *Caligus stromii*, as well as *Caligus minimus*. Notably, *L. salmonis* is found exclusively in the Northern hemisphere, while *C. rogercresseyi* holds particular significance in Chile as the most impactful sea louse species affecting the salmon industry.

Of particular significance in Mediterranean fish farming is a representative of the Lernanthropidae family: *Lernanthropus* spp. Among the species within *Lernanthropus* spp. are *Lernanthropus kroyeri, Lernanthropus callinomymicola, Lernanthropus indefinitus, Lernanthropus cynoscicola*, and *Lernanthropus gisleri*.

Of particular significance in freshwater aquaculture are parasitic copepods of the family Argulidae, with representative members of the genus *Argulus* i.e., (*A. foliaceus, A. japonicus*, and *A. coregoni*) and members of the Lernaeopodidae family, of the representative genus *Salmincola* which infest salmonids.

Fish infestation is indicated when at least one stage of a parasite is observable on the fish's surface. In specific instances, automated methods for sea lice counting may be utilized to identify and quantify infestation by counting parasites. Typically, manual/visual methods for sea lice counting can be employed to identify infestation and assess the extent of sea lice infestation by enumerating parasites.

As used herein, the term "controlling" involves diminishing the population of ectoparasites, particularly fish-parasitic crustaceans, specifically sea lice. This includes the reduction, elimination, or prevention of an initial infestation and/or further infestation, particularly targeting all parasitic stages of fish-parasitic crustaceans, especially sea lice.

As used herein, the term "treatment" refers to both proactive and responsive measures, encompassing actions such as controlling, eliminating, protecting against, and/or preventing infestation or conditions caused by fish ectoparasites, particularly fish-parasitic crustaceans, specifically sea lice, in an individual fish or a population of fish. These terms include efforts to decrease the average number of parasites, like sea lice, affecting each fish in a population, or thwarting an increase in the average number of current infestations. This involves addressing existing ectoparasite infestations, and optionally, preventing the initiation of new infestations with ectoparasites, such as sea lice, or the associated signs. Additionally, it can involve mitigating the severity of disorders, conditions, or signs linked to an ectoparasite infestation. The terms may also cover averting the recurrence of fish ectoparasite infestations or associated symptoms, as well as actions falling under "control," such as killing, repelling, expelling, incapacitating, deterring, eliminating, alleviating, minimizing, and eradicating.

As used herein, the term "effective amount" pertains to the quantity or dosage of the active ingredient, salt, N-oxide, or solvate thereof, that, upon administration as a single dose or multiple doses to a fish or a fish population, produces the intended effect. When determining the effective amount, various factors may be taken into account, including but not limited to the fish species, the extent of parasite infestation, the response of the fish population, the method of administration, the bioavailability features of the administered preparation, the chosen dosage regimen, the use of concurrent medications, and other pertinent circumstances.

As used herein, the term "composition" denotes a product containing the active ingredient, salt, N-oxide, or solvate thereof, along with a veterinary acceptable diluent, carrier, or excipient. In this context, "veterinary acceptable" implies that a component must chemically and/or toxicologically align with other ingredients in the composition or the treated fish, unless specified otherwise. The term "pharmaceutically acceptable" carries the same meaning as "veterinary acceptable." For instance, the composition may include the active ingredient, salt, N-oxide, or solvate thereof, combined with nutritionally suitable fish feed.

In some embodiments, the active ingredient, or salt, or N-oxide, or solvate thereof, described herein may be used in combination with one or more other physiologically active agents. As used herein, the term "used in combination" includes administration together with, or in the same course of, therapy with the active ingredient, or salt, or N-oxide, or solvate thereof, described herein.

Such physiologically active agents can be another antiparasitic, especially a sea louse controlling agent, an antibiotic, a vaccine component including immune enhancing agents, or a feed ingredient containing immune modifying agents. Suitable antiparasitic agents are, for example, hydrogen peroxide; formaldehyde; an organophosphate such as trichlorfon, malathion, dichlorvos or azamethiphos; a macrocyclic lactone such as ivermectin, emamectin benzoate or moxidectin; a pyrethroid such as cypermethrin, or deltamethrin; a neonicotinoid such as imidacloprid, nitenpyram, thiamethoxam or thiacloprid; a spinosyn such as spinosad; an insect growth regulator (IGR) such as epofenonane, triprene, methoprene, diflubenzuron, teflubenzuron, triflumuron, fluazuron, novaluron, or lufenuron; a carbamate such as phenoxycarb; an isoxazoline such as afoxolaner (including substantially pure active enantiomer), sarolaner, fluralaner (including substantially pure active enantiomer) and lotilaner; or a cyclopropylamide compound. These active agents are described in WO2022162001A1, U.S. Pat. No. 7,964,204, US 2010/0254960, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, 9,221,835, US 2011/0144349, U.S. Pat. No. 8,053,452; US 2010/0137612, U.S. Pat. No. 8,410,153, US2011/152081, WO 2012/089623, WO 2012/089622, U.S. Pat. Nos. 8,119,671; 7,947,715; WO2012/120135, WO 2012/107533, WO 2011/157748, US 2011/0245274, US 2011/0245239, US2012/0232026, US 2012/0077765, US 2012/0035122, US 2011/0251247, WO 2011/154433, WO2011/154434, US 2012/0238517, US 2011/0166193, WO 2011/104088, WO 2011/104087, WO2011/104089, US 2012/015946, US 2009/0143410, WO 2007/123855 A2, US 2011/0118212, U.S. Pat. Nos. 7,951,828, 7,662,972, US 2010/0137372, US 2010/0179194 A2, US 2011/0086886 A2, US 2011/0059988, US 2010/0179195, US 2015/0126523, WO 2010/003923, WO2010/003877, WO 2010/072602, WO 2014/134236, WO 2017/147352, U.S. Pat. Nos. 7,897,630, and 7,951,828, all of which are incorporated herein by reference in their entirety.

As used herein, the term "salt" refers to an acid or base salt, which is typically formed by, for example, mixing the compound with an acid or base, respectively, using various known methods in the art. To the extent a salt of the compound is intended to be administered in vivo (i.e., to an animal) for a therapeutic benefit, the salt is pharmaceutically acceptable.

As used herein, the term "solvate" refers to stable complexes of an ingredient with solvent, such that the complex remains intact after the non-complexed solvent is removed. These complexes are often referred to as "solvates." A solvate may be formed by aggregation of the active ingredient described herein with solvent molecules such as water, alcohols, for example ethanol, aromatic solvents such as toluene, ethers, halogenated organic solvents such as dichloromethane, preferably in a definite proportion by weight.

As used herein, the term "N-oxide" refers to a compound formed by oxidation of an N-atom in an amine or N-heterocycle such as pyridine and pyrimidine by oxidation agents such as hydrogen peroxide, peracids or inorganic oxidation agents such as potassium peroxymonosulfate (oxone).

EXAMPLES

The following examples describe some exemplary modes of making and practicing certain compositions that are described herein. These examples are for illustrative purposes only and are not meant to limit the scope of the compositions and methods described herein.

Example 1

Study Design

A randomized, blinded, parallel-group, negative-controlled study was conducted in which, the active ingredient was administered in medicated feed to laboratory-maintained Atlantic salmon (*Salmo salar*) post-smolts in seawater. Smolts were experimentally infested with sea lice (*Lepeophtheirus salmonis*) under laboratory conditions prior to being fed the medicated diet to assess the efficacy of the active ingredient in reducing the number of sea lice/fish.

Healthy Atlantic salmon post-smolts (n=750) were selected for enrollment and distributed sequentially across ten (10) study tanks. Fish were weighed individually during the allocation of fish to tanks on study day (SD)-95, with SD 0 serving as the first day of treatment. Fish were weighed on SD −2, +8, +18, +22, and +30. The fish weights on SD −2 were used to estimate the average weight of all fish and used to determine the feeding amount during the treatment period (SD 0−+6). A target of total of 10 fish/tank were lethally sampled, lice-counted, and weight and length were measured. The mean weight of fish in tanks on SD −2 was 829.9±161.7 g.

Atlantic salmon post-smolts were infested once with sea lice using an experimental challenge model. About 50 copepodids (*Lepeophtheirus salmonis*) per fish were added to each tank on SD −17. During the study the water temperature varied between 8 and 12° C. The water oxygen saturation was consistently above 80% throughout the study.

Five treatment groups were randomly assigned to ten study tanks so that there were 2 tanks per treatment group. Study personnel were blinded as to the identity of the treatments for each tank.

Sea lice were counted four times during the study. All sampled fish were euthanized and lice counted. The baseline count occurred on SD −2 (with 10 fish per tank), corresponding to ~160 degree days (15 d) post-infestation. The time was sufficient for lice development to the chalimus stage. Count 1 occurred on SD +8 (with 20 fish per tank) corresponding to ~260 degree days (25 d) post infestation and 2 days post treatment. The time was sufficient for lice development into chalimus and pre-adult stages in the control tanks. Count 2 occurred on SD +18 (with 20 fish per tank) corresponding to ~360 degree days (35 d) post infestation and 12 days post treatment. The time was sufficient for lice development into adult males and females in the control tanks. Count 3 occurred on SD +22 (with 20 fish per tank) corresponding to ~400 degree days (39 d) post infestation and 16 days post treatment. The time was sufficient for lice development into adult males and females with no chalimus stages present in the control tanks.

mobile category included pre-adult and adult life stages of both males and females. The numbers of mobile, attached, and total lice were considered in this study. The descriptive statistics, such as the mean, standard deviation, and percent efficacy, were computed for treatment groups at each sampling time.

Table 1 shows mean (+/−SD) number of mobile lice, attached lice and the total number of lice/fish and percent efficacy for each treatment group at each post-treatment sampling time.

TABLE 1

| DPT | Dose Rate (mg/kg/d) | Number of Mobile Lice/Fish | | Number of Attached Lice/Fish | | Total Number of Lice/Fish | |
|---|---|---|---|---|---|---|---|
| | | Mean ± SD* | % Efficacy | Mean ± SD* | % Efficacy | Mean ± SD* | % Efficacy |
| 2 | 0 | 15.1 ± 4.9 | | 3.3 ± 1.3 | | 18.4 ± 5.0 | |
| | 0.010 | 1.7 ± 2.2 | 89.1 | 0.1 ± 0.3 | 96.2 | 1.8 ± 2.4 | 90.3 |
| | 0.025 | 0.2 ± 0.3 | 98.8 | 0.1 ± 0.1 | 98.5 | 0.2 ± 0.3 | 98.8 |
| | 0.050 | 0.1 ± 0.1 | 99.7 | 0.3 ± 0.3 | 92.3 | 0.3 ± 0.3 | 98.4 |
| | 0.125 | 0.0 ± 0.1 | 99.8 | 0.2 ± 0.3 | 93.8 | 0.2 ± 0.4 | 98.8 |
| 12 | 0 | 18.5 ± 4.8 | | 0.0 ± 0.1 | | 18.6 ± 4.1 | |
| | 0.010 | 1.1 ± 3.0 | 94.1 | 0.0 ± 0.0 | — | 1.1 ± 3.0 | 94.1 |
| | 0.025 | 0.0 ± 0.1 | 99.9 | 0.1 ± 0.2 | — | 0.1 ± 0.2 | 99.5 |
| | 0.050 | 0.1 ± 0.2 | 99.6 | 0.0 ± 0.0 | — | 0.1 ± 0.2 | 99.6 |
| | 0.125 | 0.0 ± 0.0 | 100.0 | 0.0 ± 0.1 | — | 0.0 ± 0.1 | 99.9 |
| 16 | 0 | 19.3 ± 5.2 | | 0.0 ± 0.0 | | 19.3 ± 5.2 | |
| | 0.010 | 0.5 ± 0.7 | 97.7 | 0.0 ± 0.0 | — | 0.5 ± 0.7 | 97.7 |
| | 0.025 | 0.0 ± 0.1 | 99.9 | 0.0 ± 0.0 | — | 0.0 ± 0.1 | 99.9 |
| | 0.050 | 0.1 ± 0.2 | 99.7 | 0.0 ± 0.0 | — | 0.1 ± 0.2 | 99.7 |
| | 0.125 | 0.1 ± 0.2 | 99.9 | 0.1 ± 0.2 | — | 0.1 ± 0.2 | 99.6 |

*SD—standard deviation.

Medicated feed was prepared by dry coating commercially available fish feed pellets with a premix containing the active ingredient to reach a content of about 1.6, 4.0. 8.0 and 19.9 mg/kg. The fish pellets were then coated with feed grade herring fish oil at an inclusion rate of about 0.75% w/w (7.5 g/kg feed) The consumption rate of the medicated feed was set to 0.628% body weight.

Treatment efficacy was computed for total number of sea lice/fish and total number of mobile life stages, i.e., preadult & adult sea lice/fish for each post-treatment sea lice counting occasion. For the total number of attached/fish, treatment efficacy was computed at the first count post-treatment. Percent efficacy was computed using Abbott's formula for each treatment group compared to control as follows:

$$\text{percent efficacy} = 100 * (MC - MT)/MC,$$

where MC and MT are the arithmetic means of sea lice counts in the untreated control and S-roxapin-treated groups, respectively.

Treatments were considered efficacious when the percent efficacy was ≥90% for treated groups compared to untreated control groups.

Results—Activity Against *Lepeophtheirus Salmonis* on Atlantic Salmon

The mean sea lice abundance was reported for different parasite life stages (attached, mobile, and total (attached and mobile together)) and computed as the number of lice on salmon divided by the number of sampled fish per tank. The attached category included chalimus I & II stages. The These data are depicted graphically in FIGS. 1-4.

The inventors of the pending application have discovered that an unexpectedly low dose of the active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, including salts, or N-oxides, or solvates thereof, of structural formula

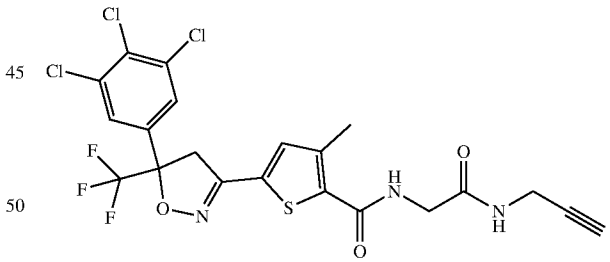

is therapeutically active against fish ectoparasite infestation (such as sea lice infestation) on fish (such as Atlantic salmon).

Example 2

Study Design

A randomized, blinded, parallel-group, negative-controlled study was conducted in which, the active ingredient was administered to Atlantic salmon at three dose rate (0 mg/kg/day, 0.025 mg/kg/day, and 0.060 mg/kg/day administered in medicated feed for 7 consecutive days. Following the treatment, the fish were intentionally infested with sea lice either 8 or 17 DPT, all within a controlled laboratory environment with seawater. The evaluation of efficacy for each cohort occurred at three specific timepoints post-infestation by comparing lice counts between the groups that received treatment and the untreated control groups.

Healthy Atlantic salmon post-smolts (n=1080) were selected for enrollment and distributed sequentially across eighteen (18) study tanks. Fish were weighed individually during the allocation of fish to tanks on study day (SD) −55&−56. Fish were weighed again on SD −19 to estimate the average weight of all fish and used to determine the feeding amount during the treatment period (SD 0−+6). The mean weight of fish prior to treatment was 716.1±152.5 g. Fish in the cohort infested 8 DPT were additionally weighed on SD +8, +14, +27, +35, +41 and +48. Fish in the cohort infested 17 DPT were additionally weighed on SD +8, +23, +36, +44, +50, and +57. For both cohorts SD 0 served as the first day of treatment.

Atlantic salmon post-smolts at each infestation time (8 or 17 DPT) were infested once with about 100 copepodids (*Lepeophtheirus salmonis*) per fish. During the study the water temperature varied between 9 and 13° C., and the water oxygen saturation was above 80%.

Three treatment groups were randomly assigned to eighteen study tanks by blocking the paired tank rows for the 8 and 17 DPT exposure. Study personnel were blinded as to the identity of the treatments for each tank.

Sea lice were counted three times during the study. The counts occurred on 21, 27, 34 days post infestation for counts I, II, and II respectively after each infestation. The counts were strategically scheduled to ensure the presence of life stages, including chalimus, pre-adult, and adult stages, in at least one of the three counts within the negative control treatment. At all timepoints 10 fish were euthanized and lice counted.

Medicated feed was prepared by dry coating commercially available fish feed pellets with a premix containing the active ingredient to reach a content of about 4.2 and 10.0 mg/kg. The fish pellets were then coated with feed grade herring fish oil at an inclusion rate of about 0.75% w/w (7.5 g/kg feed) The consumption rate of the medicated feed was set to 0.6% body weight.

For the cohort infested at 8 DPT and the cohort infested at 17 DPT, treatment efficacy was computed for total number of sea lice/fish and total number of mobile life stages, i.e., preadult & adult sea lice/fish for each sea lice counting occasion (Count I, II & III). For the total number of attached/fish, treatment efficacy was computed at Count I only. Percent efficacy was computed using Abbott's formula for each treatment group compared to control as follows:

percent efficacy=100*(*MC−MT*)/*MC*, where MC and MT are the arithmetic means of sea lice counts in the untreated control and S-roxapin-treated groups, respectively.

Treatments were considered efficacious when the percent efficacy was ≥90% for treated groups compared to untreated control groups. The mean sea lice abundance was reported for different parasite life stages (attached, mobile, and total (attached and mobile together)) and computed as the number of lice on salmon divided by the number of sampled fish per tank. The attached category included chalimus I & II stages. The mobile category included pre-adult and adult life stages of both males and females. The numbers of mobile, attached, and total lice were considered in this study.

Results:

Duration of Efficacy Against Mobile Lice

For the cohort infested at 8 DPT, the percent efficacy for mobile lice ranged across evaluation timepoints between 86.9% and 91.8% for the treatment group 0.025 mg/kg/day and between 99.2% and 100% for the treatment group 0.060 mg/kg/day in the same cohort. However, for the cohort infested at 17 DPT, only the 0.060 mg/kg/day dose showed some efficacy with percent ranging between 17.4% and 23%. The treatment dose of 0.025 mg/kg/day showed no efficacy. (Table 2).

Duration of Efficacy Against Attached Lice

Due to the practically zero attached lice counts at the second and third evaluation timepoints (due to transition into the pre-adult and adult life stages), percent efficacy was calculated only for the first evaluation timepoint. For the cohort infested at 8 DPT, the percent efficacy was 92.5% for the 0.025 mg/kg/day dose and 99.8% for the 0.060 mg/kg/day dose. For the cohort infested at 17 DPT, the percent efficacy was 21.2% and 46.2% for the 0.025 mg/kg/day and 0.060 mg/kg/day doses, respectively. (Table 2).

Duration of Efficacy Based on Total Number of Lice/Fish

For the cohort infested at 8 DPT, the percent efficacy for total sea lice was computed to be above 86.8% and above 99.2% for the 0.025 mg/kg/day and 0.060 mg/kg/day treatment groups, respectively. For the cohort infested at 17 DPT, only the treatment dose of 0.060 mg/kg/day showed some efficacy, with the percentage ranging between 17% and 23%. No efficacy was observed for the treatment dose of 0.025 mg/kg/day in DOE14 as shown in Table 2.

Table 2 shows mean (+/−SD) number of mobile lice, attached lice and the total number of lice/fish and percent efficacy for each treatment compared to the negative control group at each count (21, 27 and 34 days post infestation) for cohorts infested at 8 and 17 DPT.

TABLE 2

| Treatment group mg/kg/day | Infestation Day | Number of Mobile Lice/Fish | | Number of Attached Lice/Fish | | Total Number of Lice/Fish | |
|---|---|---|---|---|---|---|---|
| | | Mean ± SD* | % Efficacy | Mean ± SD* | % Efficacy | Mean ± SD* | % Efficacy |
| Count I (21DPI) | | | | | | | |
| 0 | 8 | 7.5 ± 3.1 | | 21.7 ± 6.4 | | 29.2 ± 6.6 | |
| | 17 | 22.1 ± 6.5 | | 3.5 ± 2.6 | | 25.6 ± 6.4 | |
| 0.025 | 8 | 1.0 ± 1.3 | 87.2 | 1.6 ± 2.0 | 92.5 | 2.6 ± 2.9 | 91.1 |
| | 17 | 24.4 ± 8.8 | −10.1 | 2.7 ± 1.9 | 21.2 | 27.1 ± 9.0 | −5.9 |
| 0.060 | 8 | 0.0 ± 0.2 | 99.6 | 0.0 ± 0.2 | 99.8 | 0.1 ± 0.3 | 99.8 |
| | 17 | 18.0 ± 6.1 | 18.5 | 1.9 ± 1.6 | 46.2 | 19.9 ± 6.1 | 22.3 |

TABLE 2-continued

| Treatment | | Number of Mobile Lice/Fish | | Number of Attached Lice/Fish | | Total Number of Lice/Fish | |
|---|---|---|---|---|---|---|---|
| group mg/kg/day | Infestation Day | Mean ± SD* | % Efficacy | Mean ± SD* | % Efficacy | Mean ± SD* | % Efficacy |
| Count II (24 DPI) | | | | | | | |
| 0 | 8 | 27.6 ± 7.5 | 86.9 | 0.1 ± 0.3 | | 27.7 ± 7.5 | |
|  | 17 | 29.9 ± 7.0 | −1.12 | 0.0 ± 0.0 | | 29.9 ± 7.0 | |
| 0.025 | 8 | 3.6 ± 3.0 | 99.2 | 0.0 ± 0.2 | — | 3.7 ± 3.1 | 86.8 |
|  | 17 | 30.2 ± 9.5 | 17.4 | 0.0 ± 0.0 | — | 30.2 ± 9.5 | −1.1 |
| 0.060 | 8 | 0.2 ± 0.5 | | 0.0 ± 0.0 | — | 0.2 ± 0.5 | 99.2 |
|  | 17 | 24.7 ± 7.0 | | 0.0 ± 0.0 | — | 24.7 ± 7.0 | 17.4 |
| Count III (34 DPI) | | | | | | | |
| 0 | 8 | 30.9 ± 8.5 | | 0.0 ± 0.0 | | 30.9 ± 8.5 | |
|  | 17 | 27.6 ± 10.5 | | 0.0 ± 0.2 | | 27.7 ± 10.5 | |
| 0.025 | 8 | 2.5 ± 2.8 | 91.8 | 0.0 ± 0.0 | — | 2.5 ± 2.8 | 91.8 |
|  | 17 | 32.1 ± 12.1 | −16.2 | 0.0 ± 0.0 | — | 32.1 ± 12.1 | −16.0 |
| 0.060 | 8 | 0.0 ± 0.0 | 100 | 0.0 ± 0.0 | — | 0.0 ± 0.0 | 100 |
|  | 17 | 21.3 ± 9.0 | 23.0 | 0.0 ± 0.0 | — | 21.3 ± 9.0 | 23.1 |

*SD—standard deviation.

These data are depicted graphically in FIGS. 5-8.

Other examples of implementations will become apparent to the reader in view of the teachings of the present description and as such, will not be further described here.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

Reference throughout the specification to "some embodiments", and so forth, means that a particular element (e.g., feature, structure, and/or characteristic) described in connection with the invention is included in at least one embodiment described herein, and may or may not be present in other embodiments. In addition, it is to be understood that the described inventive features may be combined in any suitable manner in the various embodiments.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions, will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although various embodiments of the disclosure have been described and illustrated, it will be apparent to those skilled in the art considering the present description that numerous modifications and variations can be made. The scope of the invention is defined more particularly in the appended claims.

The invention claimed is:

1. A method for treatment or control of an ectoparasite infestation on fish, comprising oral administration to the fish of active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide, or salts, or N-oxide, or solvates thereof, of structural formula

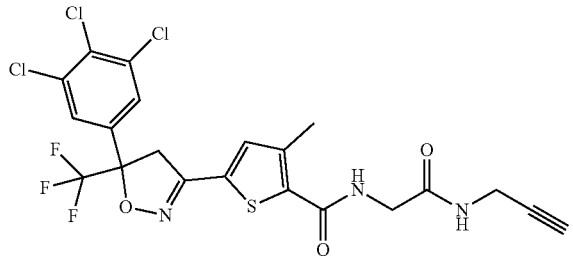 [SMILES: C#CCNC(=O)CNC(=O)c1sc(C2=NOC(c3cc(Cl)c(Cl)c(Cl)c3)(C(F)(F)F)C2)cc1C]

in a dosage of from about 0.025 mg/kg/d to about 0.250 mg/kg/d.

2. The method according to claim 1, wherein the ectoparasite infestation is a sea lice infestation.

3. The method according to claim 1, wherein the oral administration is from about 3 to about 10 consecutive days.

4. The method according to claim 1, wherein the active ingredient, or salts, or N-oxide, or solvate thereof, is comprised in a fish oral composition.

5. The method according to claim 4, wherein the fish oral composition comprises from about 0.01 wt. % to about 99 wt. % of the active ingredient, or salt, or N-oxide, or solvate thereof.

6. The method according to claim 4, wherein the fish oral composition is a medicated fish feed.

7. The method according to claim 6, wherein the medicated fish feed is a feed pellet or feed granule.

8. The method according to claim 1, wherein the dosage is of about 0.025 mg/kg/d, about 0.050 mg/kg/d, or about 0.125 mg/kg/d.

9. The method according to claim 1, wherein the fish is a salmonid.

10. The method according to claim 2, wherein the sea lice infestation involves copepodids, chalimi, pre-adults, or adults, or a combination of lice life stages in infestations.

11. The method according to claim 1, wherein the dosage is of from about 0.025 mg/kg/d to about 0.125 mg/kg/d.

12. The method according to claim 1, wherein the oral administration is during 7 consecutive days.

13. A method for treatment or control of an ectoparasite infestation on fish, comprising oral administration to the fish of active ingredient(S)-3-methyl-N-(2-oxo-2-(prop-2-yn-1-ylamino)ethyl)-5-(5-(3,4,5-trichlorophenyl)-5-(trifluoromethyl)-4,5-dihydroisoxazol-3-yl)thiophene-2-carboxamide or salts thereof, of structural formula

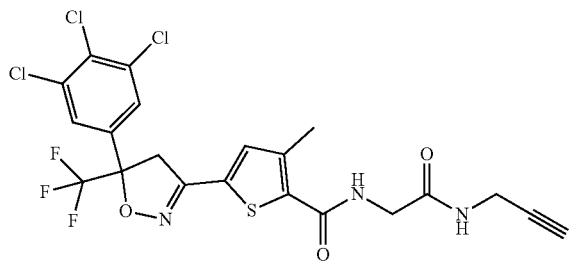 [SMILES: C#CCNC(=O)CNC(=O)c1sc(C2=NOC(c3cc(Cl)c(Cl)c(Cl)c3)(C(F)(F)F)C2)cc1C]

in a dosage of from about 0.025 mg/kg/d to about 0.125 mg/kg/d.

* * * * *

UNITED STATES PATENT AND TRADEMARK OFFICE
CERTIFICATE OF CORRECTION

PATENT NO. : 12,280,040 B2
APPLICATION NO. : 18/884300
DATED : April 22, 2025
INVENTOR(S) : Phillips Page 1 of 4

It is certified that error appears in the above-identified patent and that said Letters Patent is hereby corrected as shown below:

In the Specification

In Column 7, Line 61:
"present inventors have" should read --inventor has--.

In Table 1:

"
| DPT | Dose Rate (mg/kg/d) | Number of Mobile Lice / Fish | | Number of Attached Lice / Fish | | Total Number of Lice / Fish | |
|---|---|---|---|---|---|---|---|
| | | Mean ± SD* | % Efficacy | Mean ± SD* | % Efficacy | Mean ± SD* | % Efficacy |
| 2 | 0 | 15.1 ± 4.9 | | 3.3 ± 1.3 | | 18.4 ± 5.0 | |
| | 0.010 | 1.7 ± 2.2 | 89.1 | 0.1 ± 0.3 | 96.2 | 1.8 ± 2.4 | 90.3 |
| | 0.025 | 0.2 ± 0.3 | 98.8 | 0.1 ± 0.1 | 98.5 | 0.2 ± 0.3 | 98.8 |
| | 0.050 | 0.1 ± 0.1 | 99.7 | 0.3 ± 0.3 | 92.3 | 0.3 ± 0.3 | 98.4 |
| | 0.125 | 0.0 ± 0.1 | 99.8 | 0.2 ± 0.3 | 93.8 | 0.2 ± 0.4 | 98.8 |
| 12 | 0 | 18.5 ± 4.8 | | 0.0 ± 0.1 | | 18.6 ± 4.1 | |
| | 0.010 | 1.1 ± 3.0 | 94.1 | 0.0 ± 0.0 | --- | 1.1 ± 3.0 | 94.1 |
| | 0.025 | 0.0 ± 0.1 | 99.9 | 0.1 ± 0.2 | --- | 0.1 ± 0.2 | 99.5 |
| | 0.050 | 0.1 ± 0.2 | 99.6 | 0.0 ± 0.0 | --- | 0.1 ± 0.2 | 99.6 |
| | 0.125 | 0.0 ± 0.0 | 100.0 | 0.0 ± 0.1 | --- | 0.0 ± 0.1 | 99.9 |
| 16 | 0 | 19.3 ± 5.2 | | 0.0 ± 0.0 | | 19.3 ± 5.2 | |
| | 0.010 | 0.5 ± 0.7 | 97.7 | 0.0 ± 0.0 | --- | 0.5 ± 0.7 | 97.7 |
| | 0.025 | 0.0 ± 0.1 | 99.9 | 0.0 ± 0.0 | --- | 0.0 ± 0.1 | 99.9 |
| | 0.050 | 0.1 ± 0.2 | 99.7 | 0.0 ± 0.0 | --- | 0.1 ± 0.2 | 99.7 |
| | 0.125 | 0.1 ± 0.2 | 99.9 | 0.1 ± 0.2 | --- | 0.1 ± 0.2 | 99.6 |
"

Signed and Sealed this
Tenth Day of February, 2026

John A. Squires
*Director of the United States Patent and Trademark Office*

Should read:

| DPT | Dose Rate (mg/kg/d) | Number of Mobile Lice /Fish | | Number of Attached Lice / Fish | | Total Number of Lice / Fish | |
|---|---|---|---|---|---|---|---|
| | | Mean ± SD* | % Efficacy | Mean ± SD* | % Efficacy | Mean ± SD* | % Efficacy |
| 2 | 0 | 15.1 ± 4.9 | | 3.3 ± 1.3 | | 18.4 ± 5.0 | |
| | 0.010 | 1.7 ± 2.2 | 89.1 | 0.1 ± 0.3 | 96.2 | 1.8 ± 2.4 | 90.3 |
| | 0.025 | 0.2 ± 0.3 | 98.8 | 0.1 ± 0.1 | 98.5 | 0.2 ± 0.3 | 98.8 |
| | 0.050 | 0.1 ± 0.1 | 99.7 | 0.3 ± 0.3 | 92.3 | 0.3 ± 0.3 | 98.4 |
| | 0.125 | 0.0 ± 0.1 | 99.8 | 0.2 ± 0.3 | 93.8 | 0.2 ± 0.4 | 98.8 |
| 12 | 0 | 18.5 ± 4.8 | | 0.0 ± 0.1 | | 18.6 ± 4.1 | |
| | 0.010 | 1.1 ± 3.0 | 94.1 | 0.0 ± 0.0 | --- | 1.1 ± 3.0 | 94.1 |
| | 0.025 | 0.0 ± 0.1 | 99.9 | 0.1 ± 0.2 | --- | 0.1 ± 0.2 | 99.5 |
| | 0.050 | 0.1 ± 0.2 | 99.6 | 0.0 ± 0.0 | --- | 0.1 ± 0.2 | 99.6 |
| | 0.125 | 0.0 ± 0.0 | 100.0 | 0.0 ± 0.1 | --- | 0.0 ± 0.1 | 99.9 |
| 16 | 0 | 19.3 ± 5.2 | | 0.0 ± 0.0 | | 19.3 ± 5.2 | |
| | 0.010 | 0.5 ± 0.7 | 97.7 | 0.0 ± 0.0 | --- | 0.5 ± 0.7 | 97.7 |
| | 0.025 | 0.0 ± 0.1 | 99.9 | 0.0 ± 0.0 | --- | 0.0 ± 0.1 | 99.9 |
| | 0.050 | 0.1 ± 0.2 | 99.7 | 0.0 ± 0.0 | --- | 0.1 ± 0.2 | 99.7 |
| | 0.125 | 0.0 ± 0.1 | 99.9 | 0.1 ± 0.2 | --- | 0.1 ± 0.2 | 99.6 |

In Column 18, Line 35:
"inventors of the pending application have" should read --inventor of the pending application has--.

In Column 18, Line 63:
"three dose rate" should read --three dose rates--.

In Column 19, Line 20:
"C.," should read --C,--.

In Column 19, Line 28:
"counts I, II, and II" should read --counts I, II, and III--.

In Column 20, Line 42:
"ranging between 17% and 23%" should read --ranging between 17.4% and 23.1%--.

In Table 2 (continued):
"Count II (24 DPI)" should read --Count II (27 DPI)--.

In Tabel 2 (continued):

| Treatment group mg/kg/day | Infestation Day | Number of Mobile Lice/Fish | | Number of Attached Lice/Fish | | Total Number of Lice/Fish | |
|---|---|---|---|---|---|---|---|
| | | Mean ± SD* | % Efficacy | Mean ± SD* | % Efficacy | Mean ± SD* | % Efficacy |
| Count I (21DPI) | | | | | | | |
| 0 | 8 | 7.5 ± 3.1 | | 21.7 ± 6.4 | | 29.2 ± 6.6 | |
| | 17 | 22.1 ± 6.5 | | 3.5 ± 2.6 | | 25.6 ± 6.4 | |
| 0.025 | 8 | 1.0 ± 1.3 | 87.2 | 1.6 ± 2.0 | 92.5 | 2.6 ± 2.9 | 91.1 |
| | 17 | 24.4 ± 8.8 | -10.1 | 2.7 ± 1.9 | 21.2 | 27.1 ± 9.0 | -5.9 |
| 0.060 | 8 | 0.0 ± 0.2 | 99.6 | 0.0 ± 0.2 | 99.8 | 0.1 ± 0.3 | 99.8 |
| | 17 | 18.0 ± 6.1 | 18.5 | 1.9 ± 1.6 | 46.2 | 19.9 ± 6.1 | 22.3 |
| Count II (24 DPI) | | | | | | | |
| 0 | 8 | 27.6 ± 7.5 | 86.9 | 0.1 ± 0.3 | | 27.7 ± 7.5 | |
| | 17 | 29.9 ± 7.0 | -1.12 | 0.0 ± 0.0 | | 29.9 ± 7.0 | |
| 0.025 | 8 | 3.6 ± 3.0 | 99.2 | 0.0 ± 0.2 | --- | 3.7 ± 3.1 | 86.8 |
| | 17 | 30.2 ± 9.5 | 17.4 | 0.0 ± 0.0 | --- | 30.2 ± 9.5 | -1.1 |
| 0.060 | 8 | 0.2 ± 0.5 | | 0.0 ± 0.0 | --- | 0.2 ± 0.5 | 99.2 |
| | 17 | 24.7 ± 7.0 | | 0.0 ± 0.0 | --- | 24.7 ± 7.0 | 17.4 |
| Count III (34 DPI) | | | | | | | |
| 0 | 8 | 30.9 ± 8.5 | | 0.0 ± 0.0 | | 30.9 ± 8.5 | |
| | 17 | 27.6 ± 10.5 | | 0.0 ± 0.2 | | 27.7 ± 10.5 | |
| 0.025 | 8 | 2.5 ± 2.8 | 91.8 | 0.0 ± 0.0 | --- | 2.5 ± 2.8 | 91.8 |
| | 17 | 32.1 ± 12.1 | -16.2 | 0.0 ± 0.0 | --- | 32.1 ± 12.1 | -16.0 |
| 0.060 | 8 | 0.0 ± 0.0 | 100 | 0.0 ± 0.0 | --- | 0.0 ± 0.0 | 100 |
| | 17 | 21.3 ± 9.0 | 23.0 | 0.0 ± 0.0 | --- | 21.3 ± 9.0 | 23.1 |

CERTIFICATE OF CORRECTION (continued)
U.S. Pat. No. 12,280,040 B2

Should Read:

| Treatment group mg/kg/day | Infestation Day | Number of Mobile Lice / Fish | | Number of Attached Lice / Fish | | Total Number of Lice / Fish | |
|---|---|---|---|---|---|---|---|
| | | Mean ± SD* | % Efficacy | Mean ± SD* | % Efficacy | Mean ± SD* | % Efficacy |
| Count I (21DPI) | | | | | | | |
| 0 | 8 | 7.5 ± 3.1 | | 21.7 ± 6.4 | | 29.2 ± 6.6 | |
| | 17 | 22.1 ± 6.5 | | 3.5 ± 2.6 | | 25.6 ± 6.4 | |
| 0.025 | 8 | 1.0 ± 1.3 | 87.2 | 1.6 ± 2.0 | 92.5 | 2.6 ± 2.9 | 91.1 |
| | 17 | 24.4 ± 8.8 | -10.1 | 2.7 ± 1.9 | 21.2 | 27.1 ± 9.0 | -5.9 |
| 0.060 | 8 | 0.0 ± 0.2 | 99.6 | 0.0 ± 0.2 | 99.8 | 0.1 ± 0.3 | 99.8 |
| | 17 | 18.0 ± 6.1 | 18.5 | 1.9 ± 1.6 | 46.2 | 19.9 ± 6.1 | 22.3 |
| Count II (27 DPI) | | | | | | | |
| 0 | 8 | 27.6 ± 7.5 | | 0.1 ± 0.3 | | 27.7 ± 7.5 | |
| | 17 | 29.9 ± 7.0 | | 0.0 ± 0.0 | | 29.9 ± 7.0 | |
| 0.025 | 8 | 3.6 ± 3.0 | 86.9 | 0.0 ± 0.2 | --- | 3.7 ± 3.1 | 86.8 |
| | 17 | 30.2 ± 9.5 | -1.12 | 0.0 ± 0.0 | --- | 30.2 ± 9.5 | -1.1 |
| 0.060 | 8 | 0.2 ± 0.5 | 99.2 | 0.0 ± 0.0 | --- | 0.2 ± 0.5 | 99.2 |
| | 17 | 24.7 ± 7.0 | 17.4 | 0.0 ± 0.0 | --- | 24.7 ± 7.0 | 17.4 |
| Count III (34 DPI) | | | | | | | |
| 0 | 8 | 30.9 ± 8.5 | | 0.0 ± 0.0 | | 30.9 ± 8.5 | |
| | 17 | 27.6 ± 10.5 | | 0.0 ± 0.2 | | 27.7 ± 10.5 | |
| 0.025 | 8 | 2.5 ± 2.8 | 91.8 | 0.0 ± 0.0 | --- | 2.5 ± 2.8 | 91.8 |
| | 17 | 32.1 ± 12.1 | -16.2 | 0.0 ± 0.0 | --- | 32.1 ± 12.1 | -16.0 |
| 0.060 | 8 | 0.0 ± 0.0 | 100 | 0.0 ± 0.0 | --- | 0.0 ± 0.0 | 100 |
| | 17 | 21.3 ± 9.0 | 23.0 | 0.0 ± 0.0 | --- | 21.3 ± 9.0 | 23.1 |

--. --.